(12) United States Patent  (10) Patent No.: US 7,717,904 B2
Suzuki et al. (45) Date of Patent: May 18, 2010

(54) MANIPULATOR

(75) Inventors: Takashi Suzuki, Yokohama (JP); Kazuo Nakazawa, Yokohama (JP); Yasuhide Morikawa, Tokyo (JP); Masaki Kitajima, Tokyo (JP)

(73) Assignee: Keio University, Tokyo (JP)

( * ) Notice: Subject to any disclaimer, the term of this patent is extended or adjusted under 35 U.S.C. 154(b) by 1043 days.

(21) Appl. No.: 11/278,786

(22) Filed: Apr. 5, 2006

(65) Prior Publication Data

US 2006/0229666 A1 Oct. 12, 2006

(30) Foreign Application Priority Data

Apr. 7, 2005 (JP) ............................. 2005-111020

(51) Int. Cl.
*A61B 19/00* (2006.01)

(52) U.S. Cl. .......................................... 606/1; 606/205

(58) Field of Classification Search ................ 606/1, 606/50–52, 205–211, 39, 120, 151, 190, 606/237, 53; 623/24
See application file for complete search history.

(56) References Cited

U.S. PATENT DOCUMENTS

| | | | | |
|---|---|---|---|---|
| 5,520,678 A | * | 5/1996 | Heckele et al. ................ | 606/1 |
| 5,702,408 A | | 12/1997 | Wales et al. | |
| 6,063,103 A | * | 5/2000 | Hashiguchi ................ | 606/205 |
| 6,162,239 A | * | 12/2000 | Manhes ....................... | 606/205 |
| 6,273,887 B1 | * | 8/2001 | Yamauchi et al. ............. | 606/48 |
| 6,391,043 B1 | * | 5/2002 | Moll et al. ................... | 606/174 |
| 6,419,675 B1 | * | 7/2002 | Gallo, Sr. ...................... | 606/46 |
| 6,551,316 B1 | * | 4/2003 | Rinner et al. ................. | 606/57 |
| 6,554,844 B2 | * | 4/2003 | Lee et al. ..................... | 606/130 |
| 6,582,450 B2 | * | 6/2003 | Ouchi ......................... | 606/205 |
| 6,599,309 B1 | * | 7/2003 | Gilman ........................ | 606/205 |
| 6,656,205 B1 | * | 12/2003 | Manhes ....................... | 606/205 |
| 6,712,825 B2 | * | 3/2004 | Aebi et al. ................... | 606/90 |
| 6,767,349 B2 | * | 7/2004 | Ouchi .......................... | 606/51 |
| 2004/0162547 A1 | | 8/2004 | Wallace et al. | |

FOREIGN PATENT DOCUMENTS

| | | |
|---|---|---|
| JP | 2004-089482 | 3/2004 |
| JP | 2004-105451 | 4/2004 |
| JP | 2004-187798 | 7/2004 |
| WO | WO97/43943 | 11/1997 |

\* cited by examiner

*Primary Examiner*—Henry M Johnson, III
*Assistant Examiner*—Jeffrey B Lipitz
(74) *Attorney, Agent, or Firm*—Lucas & Mercanti, LLP

(57) ABSTRACT

The manipulator has two-degree-of-freedom of rotation and gripping, and is capable of ensuring force feedback or force sensation with excellent operationability. A link mechanism 3 is provided between an operation part 1 and a working part 2. The link mechanism 3 has four driving rods 3a to 3d and first and second coupling members of the sane structure, 41, 42 provided at opposite ends of the driving rods. First and second working members 2a, 2b move correspondingly to the operation of first and second operating members 1a, 1b with the aid of the link mechanism 3. The first and second working member can open and close, change the yaw angles and the pitch angles in response to the same action of the first and second operating member through the link mechanism.

12 Claims, 18 Drawing Sheets

(a)

(b)

(a)

(b)

(a)

(b)

(a)

(b)

MANIPULATOR

CROSS-REFERENCE TO RELATED APPLICATION

This is the priority-claiming application with reference to JP2005-111020 filed on Apr. 7, 2005, based upon U.S. Patent Law, the Article 119 on claiming foreign priority. The following U.S. patent application is hereby incorporated by reference in its entirety as though fully and completely set forth herein: JP2005-111020, filed on Apr. 7, 2005.

BACKGROUND OF THE INVENTION

1. Field of the Invention

The present invention relates to a multiple freedom manipulator preferable to forceps for use in low invasion operation or the like.

2. Description of the Related Art

Low invasion operations attract many attentions in the field of medical operation and have been introduced into the same in recent years. Although in conventional operations a body of a patient is largely cut as in abdominal surgery the low invasion operation is an operation which is realized only by cutting a body as possible as slightly and in which an operator treats a diseased part by inserting an elongated rod-shaped forceps and a surgical knife while observing the diseased part mainly with the aid of an endoscope.

The low invasion operation cures diseases by inserting an elongated rod-shaped forceps and a surgical knife from a small hole while watching a diseased part using an endoscope as described above, so that any damage of a normal portion can be reduced to make a contribution to patients, but, on the one hand, there are problems to make difficult the operation of a treatment tool because the tool is restricted by the hole. To solve the problem a forceps capable of moving the tip end of the forceps are now in studies and developments.

As treatment tools having flexibility at the tip end of a forceps there have been hitherto proposed a forceps disclosed in reference 1 having one-degree-of-freedom of rotation without actuator and a master/slave forceps disclosed in reference 2 having two-degree-of-freedom and gripping.

However, in order to take an arbitrary attitude the tip end of the forceps requires two or more-degree-of-freedom so that the forceps disclosed in reference 1 does not provide enough operationability.

Further, the forceps disclosed in reference 2 suffers from a difficulty that introduction and operation thereof are difficult in view of the magnitude and costs thereof and a difficulty that satisfactory force feedback cannot be obtained. For this, the forceps is unlikely to be adopted because a space in an operating room is insufficient as well as excessive force might be applied to the forceps because no enough force is transmitted thereupon.

There are known an integrated master/slave forceps disclosed in reference 3 and a forceps disclosed in reference 4 as those having two-degree-of-freedom and being smaller than that disclosed in reference 2.

Although it is intended the integrated master/slave forceps disclosed in reference 3 is miniaturized by driving only two-degree-of-freedom of rotation and the gripping of the tip end of the forceps, it requires external devises such as a power supply and a support mechanism and it has no feedback of force with respect to the freedom driven by a DC motor.

Further, the forceps disclosed in reference 4 suffers from a difficulty where rotary axes of the two-degree-of-freedom of rotation of the tip end of the forceps do not intersect to lower operationability, and has the possibility that a link swells out at the time of bending in view of the structure thereof to wind organs etc. outside a view of an endoscope. Moreover, when notice is taken of only a mechanism of adding two-degree-of-freedom on the tip end of the forceps, although there are known those disclosed in reference 5 other than those disclosed above and those disclosed in reference 6, they employ a wire to cause a severe influence of static friction and also have low rigidity of a member for transmitting power.

Reference 1: U.S. Pat. No. 5,702,408 Specification

Reference 2: International Publication WO97/43943 Pamphlet

Reference 3: Japanese Unexamined Patent Publication No.2004-105451

Reference 4: Japanese Unexamined Patent Publication No. 2004-89482

Reference 5: Japanese Unexamined Patent Publication No. 2004-187798

Reference 6: U.S. Pat. application No. 2004/0162547

Although various forceps have been proposed heretofore as described above, the forceps disclosed in reference 1 can not offer satisfactory operationability, and the one disclosed in reference 2 is difficult in its introduction and operation from the viewpoint of the size and cost, and does not present satisfactory force feedback.

Further, the forceps disclosed in reference 3 requires external apparatuses such as a power supply and a support mechanism with no force feedback, and the forceps disclosed in reference 4 has lower operation property and allows a link to be swelled outside upon its bending.

In contrast, those disclosed in references 5, 6 suffer from a severe influence of static friction and has lower rigidity of a member for transmitting power.

Since the low invasion operations require a high technique of operators, a forceps having higher operationability is desired, and a forceps having two-degree-of-freedom rotation and gripping freedom at the tip end of the forceps and being excellent in operationability and simple in maintenance and operation is strongly desired. There are however not proposed hitherto ones satisfying such requirements.

SUMMARY OF THE INVENTION

It is therefore an object of the present invention to provide a manipulator preferable to application to forcipes or the like having two-degree-of-freedom rotation and gripping freedom, being capable of obtaining satisfactory force feedback, and being excellent in operationability and simple in maintenance and operation.

The manipulator in the present invention having rotation two-degree-of-freedom of rotation and gripping freedom in the present invention is constituted as follows:

(1) In the manipulator including a working part for implementing a work and an operating part for implementing an operation, the operation in the operating part being transmitted to the working part, and force acted on the working part being transmitted to the operating part as force sensation, at least four driving rods are provided between the working part and the operating part, and opposite ends of the driving rod are coupled with the working part and the operating part via coupling members of the same structure.

Longitudinal axes of the respective driving rods are directed in parallel and at least longitudinal axes of all the driving rods being arranged not to be on the same plane, and the coupling members on the sides of the operating part and the working part forcing the respective driving rods to be moved axially in conformity with the operation of the operating part while keeping them in parallel and driving the working part correspondingly to the operation of the operating part.

(2) In (1), the operating part is comprised of the first and second operating members, and the first and second operation members are coupled rotatably with the coupling member around the central axis of the coupling member on the operating part side. The working section is comprised of the first and second working members, and the first and second working members are coupled rotatably with the coupling member on the working part side around the central axis of the coupling member.

At least first and third driving members of the foregoing driving rods are coupled with a one side of the coupling member with respect to the foregoing central axis respectively independently rotatably, and at least second and fourth driving members of the foregoing driving rods are coupled with the other side of the coupling member with respect to the foregoing central axis respectively independently rotatably.

Further, the foregoing first operating member is coupled with a first working member via first and second driving rods of the four driving rods, and the second operating member is coupled with the second working member via third and fourth driving rods among the four driving rods.

When it is assumed that an axial direction of the driving rod is X-axis, axes perpendicular to the X-axis are Y-axis and Z-axis, the manipulator constructed as above operates as follows:

(i) When the first and second operating members of the foregoing operating part are both rotated around the Y-axis, at least the first and second driving rods among the four driving rods is rotated via the coupling member in a first direction, and the third and fourth driving rods among the driving rods move oppositely to the first direction to rotate the first and second working members of the working part around the Y-axis;

(ii) when the first and second operating members of the operating part are both rotated around the Z-axis, at least the first and third driving rods among the four driving rods are both rotated in the first direction, and the second and fourth driving rods among the driving rods move oppositely to the first direction to rotate the first and second working members of the working part;

(iii) when the first operating member of the operating part is rotated around the Z-axis, one of the first and second driving rods is rotated in the first direction, and the other moves oppositely to rotate the first working member of the working part around the Z-axis; and further When the second operating member of the operating part is rotated around the Z-axis, one of the third and fourth driving rods are rotated in the first direction, and the other moves oppositely to the first direction to rotate the second working member of the working part around the Z-axis.

(3) In the descriptions (1), (2), it is possible to construct the coupling member as follows:

The coupling member provided on the operating part side and the working part side includes first and second movable members rotatable around the central axis of the coupling member, and at least the two first and second driving rods among the driving rods are mounted on opposite sides of the central axis of the first movable member rotatably around an axis parallel to the central axis and around an axis perpendicular to the central axis and a longitudinal axis of the driving rod for the first movable member.

At least the other third and fourth driving rods among the driving rods are mounted on opposite sides of the central axis of the second movable member rotatably around an axis parallel to the central axis and around an axis perpendicular to the central axis and a longitudinal axis of the driving rod for the second movable member.

Further, the first and second movable members of the coupling member provided on the working part side are coupled with the first and second working members provided on the working part, and the first and second movable members provided on the coupling member on the operating part side are coupled with the first and second operating members provided on the operating part.

(4) In the descriptions (1) to (3), a coupling member having the same structure as that of coupling members provided on the operating part side and on the working part side is provided between the working part and the operating part of the driving rod.

(5) At least one among the coupling members in (4) is attached to a fixing member attached to the casing. A central axis of the coupling member is attached to the fixing member rotatably around the central axis, and the fixing member is attached to the casing rotatably around the Y-axis.

(6) In the descriptions (1) to (5), a link mechanism is attached to tip ends of the first and second working members provided at the working part, and the tip end of the link mechanism is assumed to be the third and fourth working members for gripping any article.

The link mechanism comprises: the third working member rotating around a first rotation axis parallel to the rotation axis of the first working member of the working part; the fourth working member rotating around a second rotation axis parallel to the rotation axis of the second working member of the working part; a first arm rotatably attached to one end of the third working member at one end thereof and attached rotatably to the first working member at the other end thereof; and a second arm attached rotatably to a one end of the fourth working member at a pone end thereof and attached rotatably to the second working member at the other end thereof. A configuration of the rotation axis of the first working member, the first rotation axis, and rotation axes of opposite ends of the first arm connected through straight lines, and a configuration of the rotation axis of the second working member, the second rotation axis, and rotation axes of opposite ends of the second arm connected through straight lines are made rectangle respectively.

In accordance with the present invention the following effects are ensured:

(1) It is possible to realize a manipulator having operationability of a master/slave manipulator; simplicity in maintenance and operation of a manipulator without use of an actuator, and force feedback Particularly, the manipulator has the total of seven-degree-of-freedom by adding two-degree-of-freedom of rotation and gripping, to the four-degree-of-freedom possessed by conventional forceps, while it takes arbitrary position and attitude.

Further, the manipulator employs the link mechanism composed of the driving rods, which has higher rigidity than a wire structure adopted in many cases by a robot forceps or the like.

It is therefore possible to apply the manipulator of the present invention to forceps for cases of diseases to which no low invasion operation was applied hitherto in view of the costs and difficulty of the technique. It becomes possible to extend the range of the low invasion operation.

(2) The manipulator of the present invention is a mechanism which is constituted only by a link where axes of two-degree-of-freedom rotation at the tip end of the manipulator intersect at one point, so that it offers high operationability.

There is no possibility that any part of an organ might be caught up by the bulked link upon its bending. For example, even though the manipulator is applied to a forceps for use in endoscope operation, any organ might not be caught up.

(3) It is possible to improve the rigidity between the operating part and the forceps tip end by providing a coupling member in the middle of the driving rod and to deal with the length of the driving rod even if it is increased.

(4) It is possible to reduce the speed of the tip end of the link mechanism and hereby increase applied force by mounting the link mechanism on the tip end of the working member and gripping an object with the tip end of the link mechanism. It is therefore possible to increase gripping force and hence improve operationability upon gripping a needle or the like at the tip end of a forceps for example.

Further, it is possible to shift a rotation article and a gripping axis and hence improve operationability by providing the link mechanism. It is also possible to increase force and so reduce an influence of friction.

DETAILED DESCRIPTION OF THE INVENTION

In what follows, an embodiment of the present invention will be described. Although in the following there will be described a case where the present invention is applied to a multi-degree of freedom forceps for operations, it is applicable to manipulators for various applications in each of which it includes an operating part and a working part and the working part is operated in response to the operation of the operating part for various works.

Figure 1:
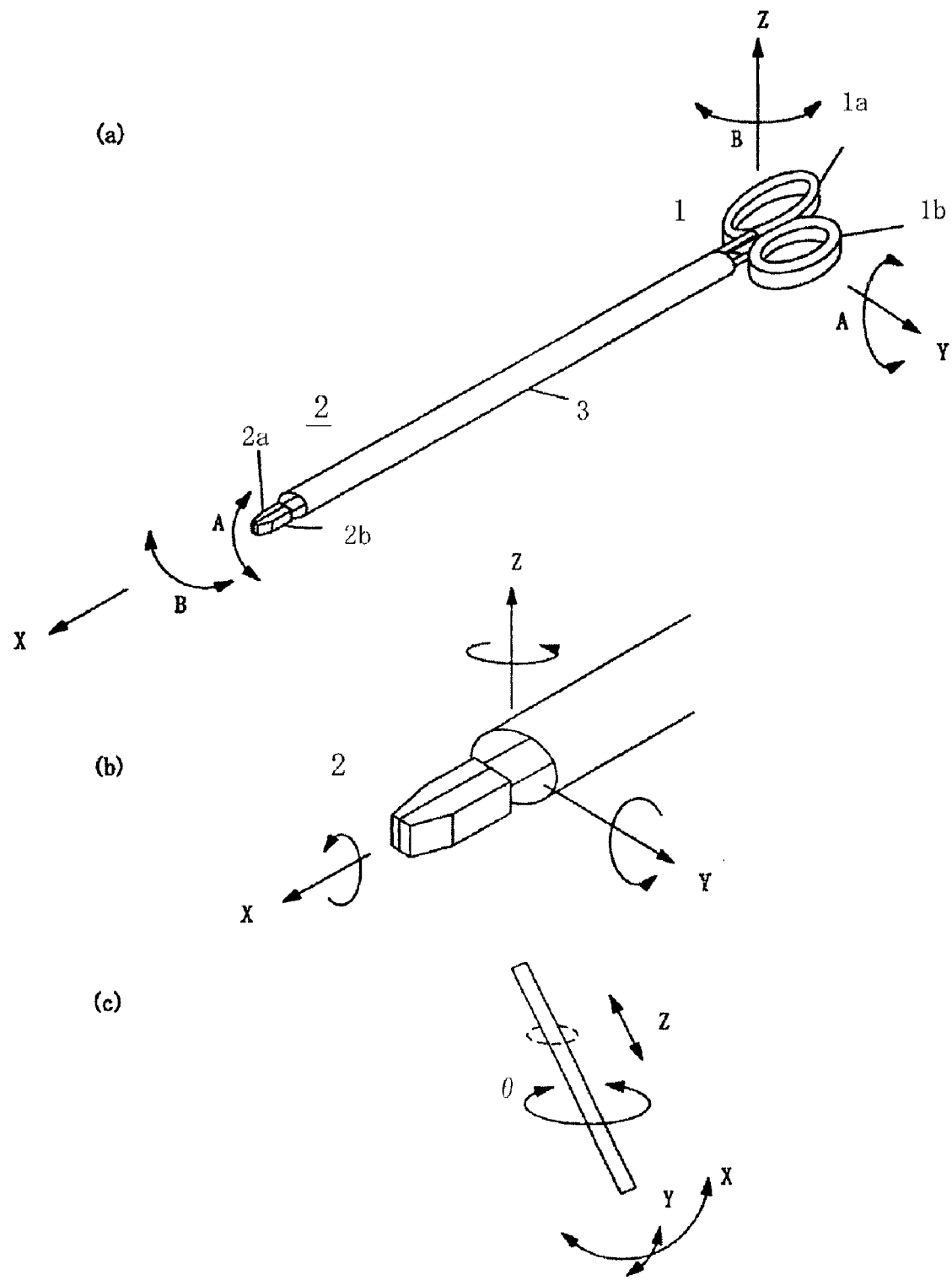
FIG. 1 is a view illustrating the schematic constitution and the degree of freedom of a forceps of an embodiment of the present invention.

Referring to FIG. 1 there are illustrated a schematic constitution of a forceps of the embodiment of the present invention and the degree of freedom in the forceps. And the degree of freedom of the forceps of the embodiment will be described.

In (a) of the same figure, designated at 1 is an operating part and 2 is a working part. The operating part 1 comprises first and second operating parts 1a, 1b, and the working part 2 comprises first and second working members 2a, 2b.

The operating part 1 and the working part 2 are coupled with a link mechanism 3 described later, and the first and second working members 2a, 2b of the working part 2 can be moved in response to the operation of the operating part 1 by controlling the first and second operating members 1a, 1b with a hand for example.

It is herein assumed that an axial direction of the link mechanism 3 provided between the operating part 1 and the working part 2 is X-axis and directions perpendicular to X-axis are Y-axis and Z-axis. When the operating part 1 is rotated around Y-axis as shown by an arrow A in the same figure, a movement of the operating part 1 is transmitted to the working part 2 via the link mechanism 3, and the working part 2 is also rotated in the direction of the arrow A in the same figure.

Further, when the operating part 1 is rotated around Z-axis as shown by an arrow B in the same figure, a movement of the operating part 1 is transmitted to the working part 2 via the link mechanism 3, and the working part 2 is also rotated as shown by the arrow B in the same figure.

Furthermore, when the first and second operating members 1a, 1b of the operating part 1 are opened and closed, the movement of the operating part 1 is transmitted to the working part 2 via the link mechanism 3, and the first and second working members 2a, 2b of the working part 2 are also opened and closed. It is usual in the forceps that the working part 2 is constructed in many cases as a gripping part for gripping an article. So, in the following, the opening and closing of the first and second working members 2a, 2b shall be referred to also as gripping, and the working part 2 as a gripping part.

In the following, the rotation around Y-axis shall be referred to as pitch as shown in FIG. 1(b), the rotation around Z-axis as yaw and the rotation around X-axis as roll.

As described above, the forceps of the present embodiment has additionally two-degree-of-freedom of rotation+freedom of gripping to the freedom possessed by conventional forceps. In contrast, when a conventional forceps with a tip end serving as only gripping is used for a low invasion operation, as shown in FIG. 1(c), a movement of the forceps is restricted by a hole, so that it has only four-degree-of-freedom, namely, thrust movement of the forceps along Z axis, rotation of the shaft around Z axis, and sway movement of the tip end in two directions along X or Y axis.

More specifically, the forceps of the present embodiment has the total of six-degree-of-freedom+gripping because it has the two-degree-of-freedom (pitch and yaw)+the freedom of gripping, as described above, additionally to the four-degree-of-freedom possessed by an ordinary forceps.

It is therefore possible for the tip end of the forceps to take an arbitrary position and attitude by making use of the forceps of the present embodiment.

It is general that a complicated work, particularly a stitching work is difficult in low invasion operation. However, provided that a forceps has a freedom at the tip end thereof, works are possible from an angle which is difficult to be taken by conventional forceps, and stitching works are also facilitated. The four-degree-of-freedom possessed by conventional forceps substantially corresponds to a movement of an arm of an operator, and the additional two-degree-of-freedom of the tip end of the forceps substantially corresponds to a wrist of an operator. It is therefore possible to also understand an effect of imparting greater freedom to the tip end of the forceps.

The forceps of the present embodiment directly controls the freedom of the tip end (working end) via the link mechanism 3, so that the force equal to that of the conventional forceps is transmitted to an operator. Further, the forceps of the present embodiment includes no electric circuit and actuator resulting in a simplified constitution, so that it is advantageous in costs and further, also in its introduction and operation it has no influence on other curing tools and diagnostic tools because they are not equipped with any electrical portion and so does not require any new external apparatus such as a power supply.

Figure 2:
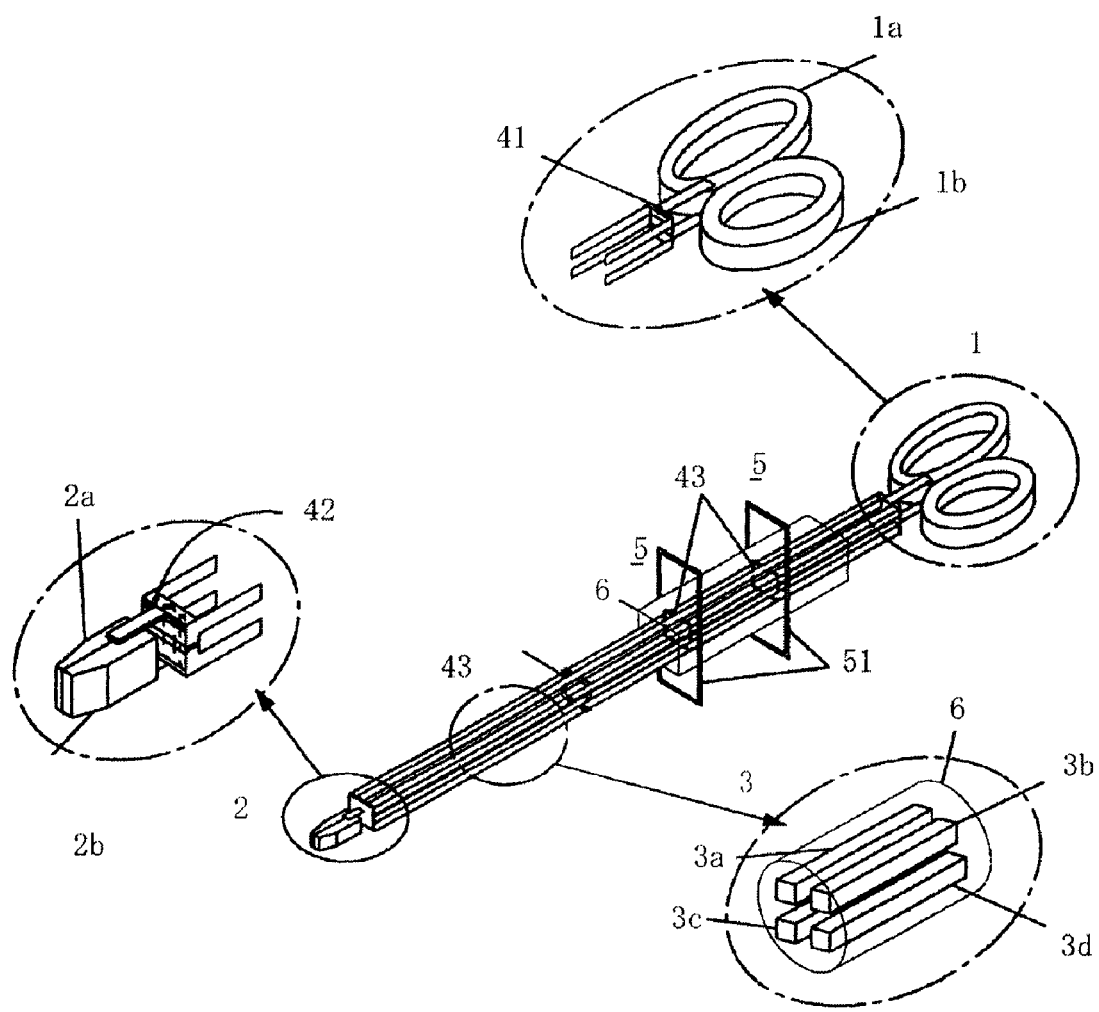
FIG. 2 is a view illustrating the entire constitution of the forceps of the embodiment of the present invention.

Referring now to FIG. 2 there is illustrated the entire constitution of the forceps of the embodiment of the present invention.

In the same figure, designated at 1 is a operating part composed of a first operating member 1a and a second operating member 1b, and 2 is a working part (gripper part) composed of a first working member 2a and a second working member 2b.

In between the operating part 1 and the working part 2 a link mechanism 3 is provided as described previously, and the link mechanism 3 comprises four driving rods 3a to 3d and first and second coupling members 41, 42 of the same structure provided at opposite ends of the driving rod.

The first and second working members 2a, 2b of the working part 2 move corresponding to the control of the first and second operating members 1a, 1b of the operating part 1 mediating the link mechanism 3.

The forceps of the present embodiment has the total seven degree-of-freedom (six-degree-of-freedom+gripping), i.e., the freedom of yaw, pitch, and gripping as described above, additionally to four-degree-of-freedom obtained by moving the whole forceps.

More specifically, once the first and second operating members 1a, 1b are opened and closed, the first working member 2a and the second working member 2b are opened and closed (gripping). Further, when yaw angles of the first and second operating members 1a, 1b are changed, yaw angles of the working members 2a, 2b are also correspondingly changed. Similarly, once pitch angles of the first and second operating members 1a, 1b are changed, pitch angles of the working members 2a, 2b are also correspondingly changed.

Designated at 5 in FIG. 2 is a fixing member described later, and the fixing member 5 consists of a coupling member 43 having the same structure as that of the coupling members 41, 42 and of fixing frame 51 for fixing the driving rods 3a to 3d such that the respective driving rods 3a to 3d are prevented from moving in a direction perpendicular to the axes of the driving rods 3a to 3d with respect to the casing (external frame 6 for covering the circumference of the driving rods) while allowing the movement of the driving rods 3a to 3d in the direction X.

Provided that the length of the forceps in the direction X is increased, the driving rods 3a to 3d are bent as force is applied thereto for example, so that there is the possibility that control force of the operating part 1 might be prevented from being transmitted correctly to the working part 2, and force applied to the working part 2 might be prevented from being correctly transmitted as inner force sense to the operating part 1.

It is possible to reduce an influence of the bending etc. of the driving rods 3a to 3d even if the length of the forceps in the direction X is increased by providing the fixing member 5 including the coupling member 43 in the way of the driving rods 3a to 3d as described above.

Instead of providing both coupling member 43 and the fixing frame 51, only the coupling member 43 may be provided at some points of the driving rods 3a to 3d. In this case, although it is possible to reduce an influence of bending etc. of the driving rods 3a to 3d, it is impossible to prevent the driving rods 3a to 3d from moving toward perpendicular to the axis of the external frame 6 due to the absence of the fixing frame 51.

Figure 3:
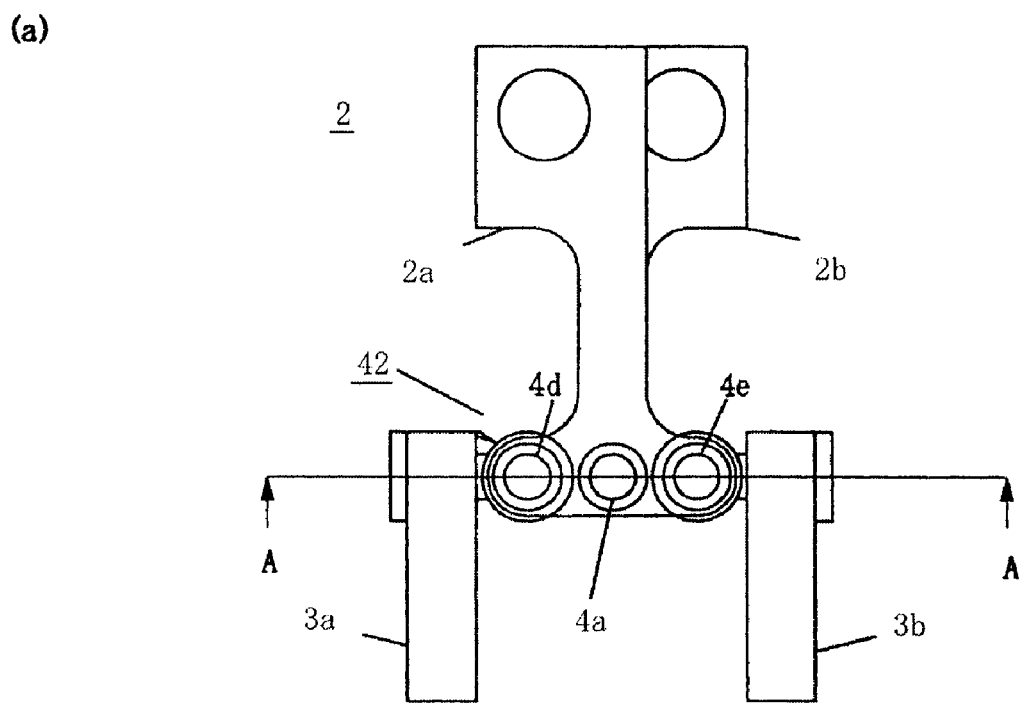
FIG. 3 is a view illustrating an exemplary constitution of a coupling member provided on the side of a working part.
Figure 3:
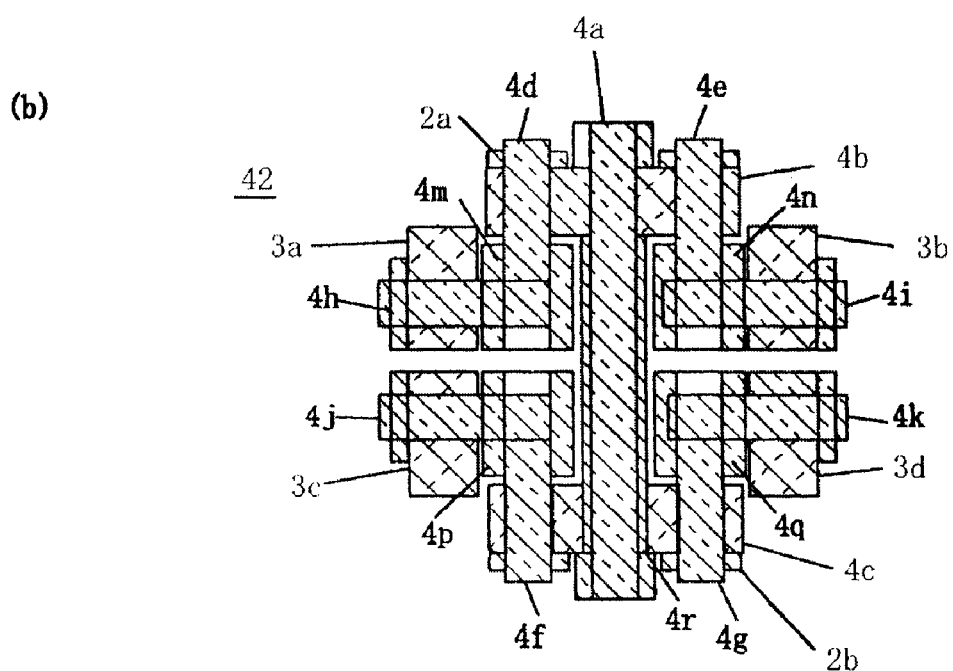

Referring to FIG. 3, there is illustrated an exemplary constitution of the coupling member 42 provided on the side of the working part, with the same figure (a) that is a view of the working part 2 viewed from the direction of Z-axis and with (b) that is a cross sectional view taken along a line A-A of (a).

In the same figure (a), (b), designated at 2a, 2b are the first and second working members (there are partly shown the working members 2a, 2b in the same figure).

Designated at 3a, 3b are the driving rods. The driving rods 3c, 3d are hidden behind lower portions of the driving rods 3a, 3b and not seen in the same figure (a).

The first working member 2a is coupled to the first movable member 4b mounted on the central shaft 4a, and the second working member 2b is coupled to the second movable member 4c mounted on a shaft member 4r rotatable with respect to the central shaft 4a.

On the opposite sides of the central shaft 4a of the first movable member 4b there are mounted rotatably a first rotary shaft 4d parallel, in axial direction, to the central shaft 4a and a second rotary shaft 4e.

A first fixing member 4m is mounted on the first rotary shaft 4d, and a first driving rod support shaft 4h perpendicular, in its axial direction, to the central shaft 4a is mounted on the same. The driving rod 3a is mounted rotatably on the first driving rod support shaft 4h.

Further, on the second rotary shaft 4e there are mounted a second fixing member 4n and a second driving rod support shaft 4i perpendicular, in axial direction, to the central shaft 4a. The driving rod 3b is mounted rotatably on the second driving rod support shaft 4i.

Similarly, there are mounted rotatably on the opposite sides of the central shaft 4a of the second movable member 4c a third rotary shaft 4f parallel, in axial direction, to the central shaft 4a and a fourth rotary shaft 4g.

On the third rotary shaft 4f there are mounted a third fixing member 4p and a third driving rod support shaft 4j perpendicular, in axial direction, to the central shaft 4a. The driving rod 3c is mounted rotatably on the third driving rod support shaft 4j.

Further, on the fourth rotary shaft 4g there are mounted a fourth fixing member 4q and a fourth driving rod support shaft 4k perpendicular, in its axial direction, to the central shaft 4a. The driving rod 3d is mounted rotatably on the fourth driving rod support shaft 4k.

The coupling member 42 has the constitution described above, wherein once the driving rod 3a moves from the background of FIG. 3(b) to foreground and the driving rod 3b moves from the foreground to the background, the first movable member 4b rotates around the central shaft 4a and the first working member 2a rotates in the left direction of FIG. 3(a). Similarly, once the driving rod 3d moves from the background of FIG. 3(b) toward the foreground and the driving rod 3c moves from the foreground toward the background, the second movable member 4c rotates around the central shaft 4a and the second working member 2b rotates in the right direction in the same figure. More specifically, once the first and second working members 2a, 2b are opened and the driving rods 3a to 3d move oppositely to the above description, the first and second working members 2a, 2b are closed.

Once the driving rods 3a, 3b move from the foreground of FIG. 3(b) toward the background and the driving rods 3c, 3d move from the background toward the foreground, the central shaft 4a is inclined such that an upper side thereof becomes the background and a lower side thereof becomes foreground of FIG. 3(b). The first and second working members are inclined, and their tip end sides correspondingly move to the background in the same figure. Once the driving rods 3a to 3d move oppositely to the above description, their tip end sides move to the foreground in FIG. 3(a).

Additionally, once the driving rods 3a, 3c move from the foreground in FIG. 3(b) toward the background and the driving rods 3b, 3d move from the background toward the foreground, the first and second movable members 4b, 4c are rotated around the central shaft 4a, and the first and second working members 2a, 2b are rotated in the right direction in FIG. 3(a). Once the driving rods 3a to 3d move oppositely to the above description, the first and second working members 2a, 2b are rotated in the left direction in FIG. 3(a).

Figure 4:
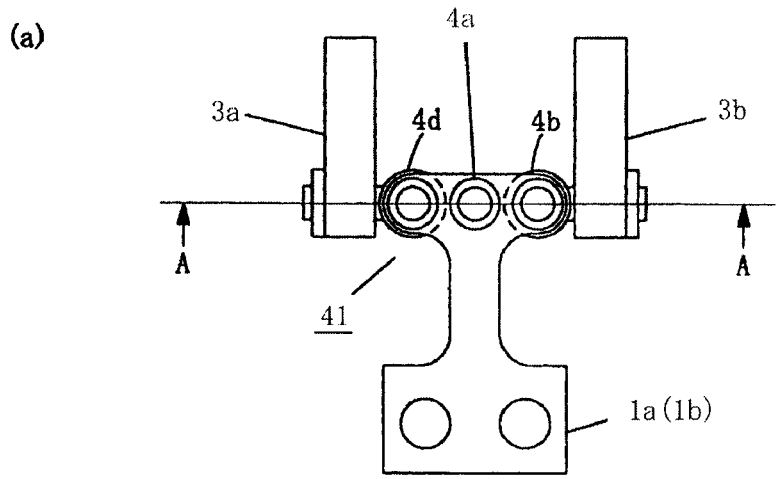
FIG. 4 is a view illustrating an exemplary constitution of a coupling member provided on the side of an operating part.
Figure 4:
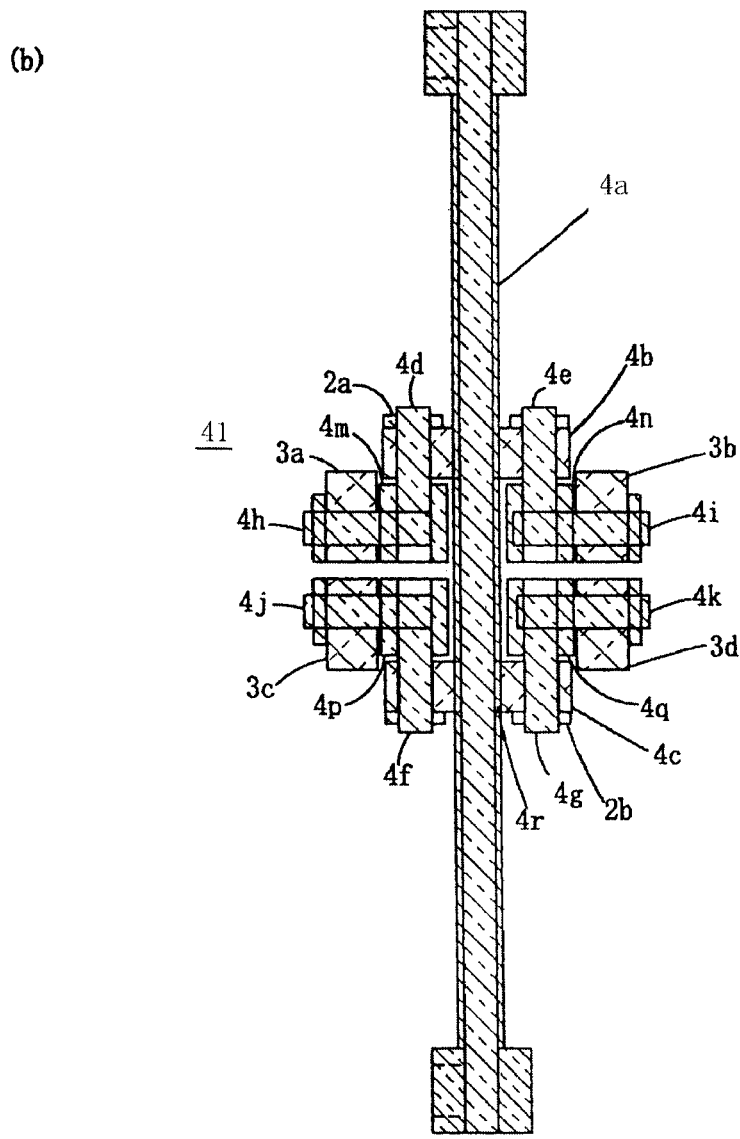

Referring to FIG. 4 there is illustrated an exemplary constitution of the coupling member 41 provided on the side of the operating part with the same figure (a) that is a view illustrating the working part 2 viewed from the Z-axis direction and (b) a cross sectional view taken along a line A-A in (a).

The structure of the coupling member provided on the side of the operating part has the same constitution as the coupling member illustrated in FIG. 3 excepting the central shaft 4a being long, and the same symbols shall be applied to the same portions.

In FIG. 4(a), designated at 1a, 1b are first and second operating members (in the same figure the operating members 1a, 1b are partly shown), and in the same figure the second operating member 1b is hidden behind a lower side of the first control member 1a.

In FIG. 4(a), (b), once the first operating member 1a is rotated to the right side, the first movable member 4b is rotated around the central shaft 4a to cause the driving rod 3a to move from the background in FIG. 4(b) toward the foreground and the driving rod 3b to move from the foreground toward the background. Hereby, the first working member 2a on the side of the working part 2 is rotated to the left side as described previously.

Similarly, once the second operating member 1b is rotated to the left side, the driving rod 3d moves from the background in FIG. 3(b) to the foreground and the driving rod 3c moves from the foreground to the background. Hereby, the second working member 2b on the side of the working part 2 is rotated to the right side.

Further, once the first operating member 1a and the second working member 1b are turned to an upper side in FIG. 4(b), the central shaft 4a is tilted to move the driving rods 3a, 3b from the foreground to the background and move the driving rods 3c, 3d from the background to the foreground of the same figure. Hereby, the tip ends of the first and second working members 2a, 2b on the side of the working part 2 are tilted to a lower side in FIG. 3(b).

Additionally, once the first operating member 1a and the second working member 1b are turned to the left side in FIG. 4(a), the first and second movable members 4b, 4c are turned around the central shaft to move the driving rods 3a, 3c from this side on the space to the interior and move the driving rods 3b, 3d from the background to the foreground in FIG. 4(b). Hereby, the tip ends of the first and second working members 2a, 2b on the side of the working part 2 are turned to the right as described previously.

Figure 5:
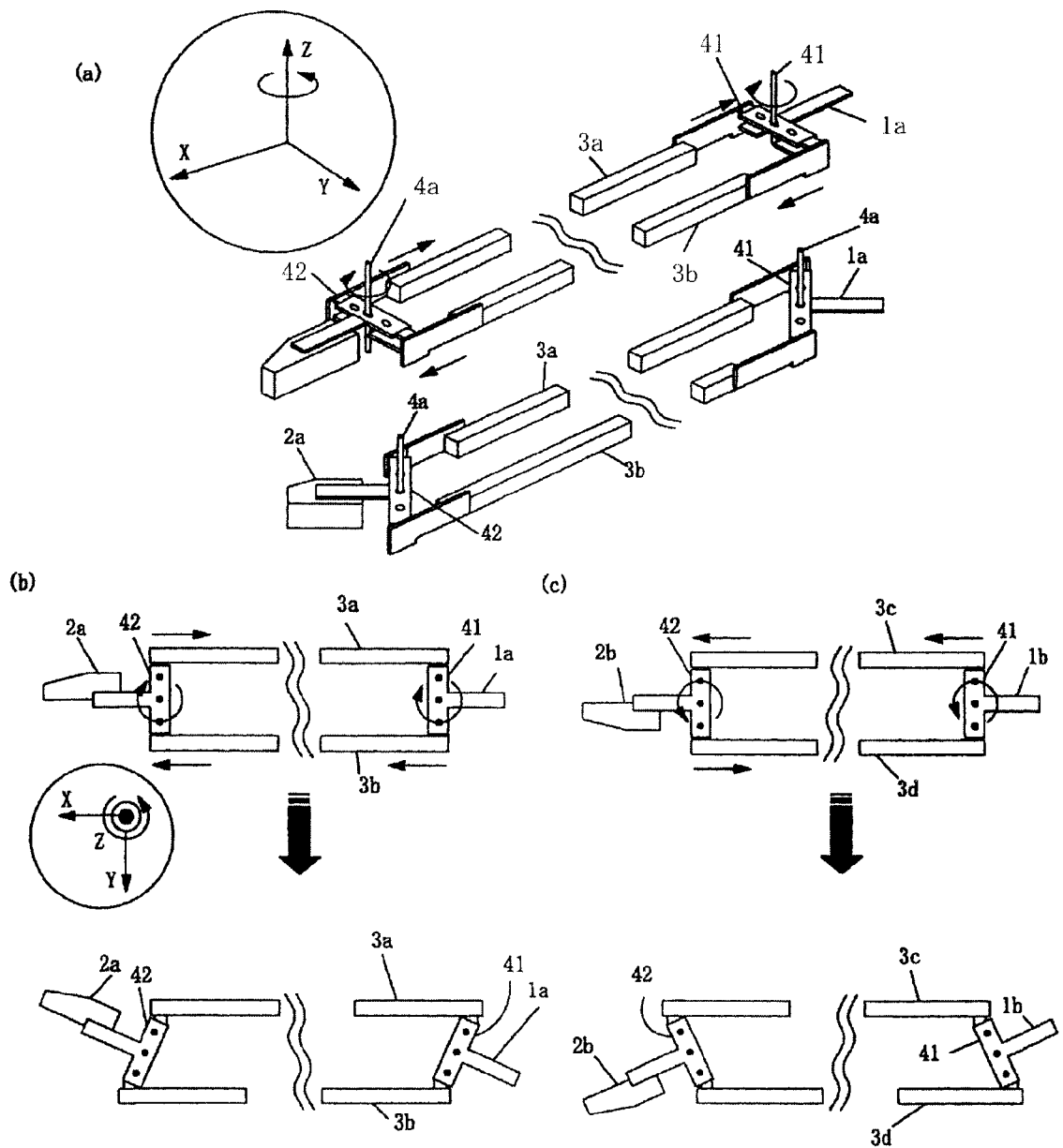
FIG. 5 is a view (1) illustrating a movement of the forceps of the embodiment of the present invention.
Figure 6:
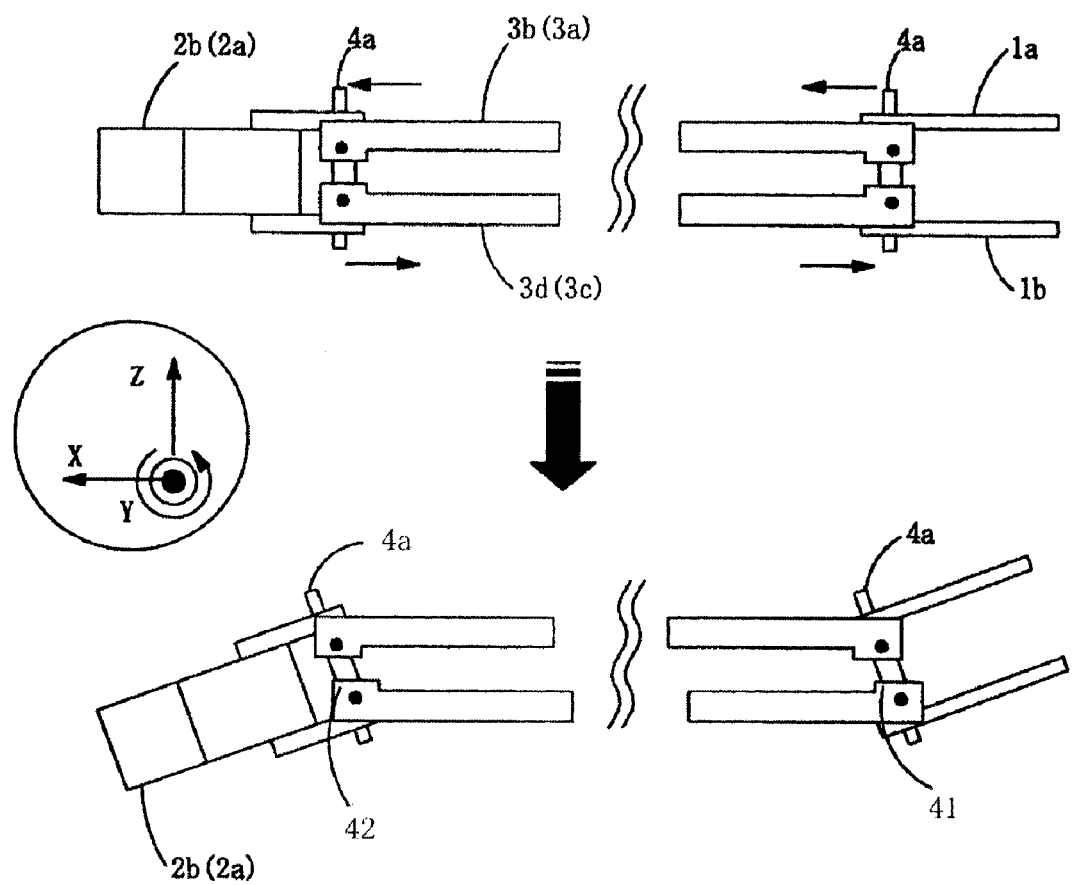
FIG. 6 is a view (2) illustrating a movement of the forceps of the embodiment of the present invention.
Figure 7:
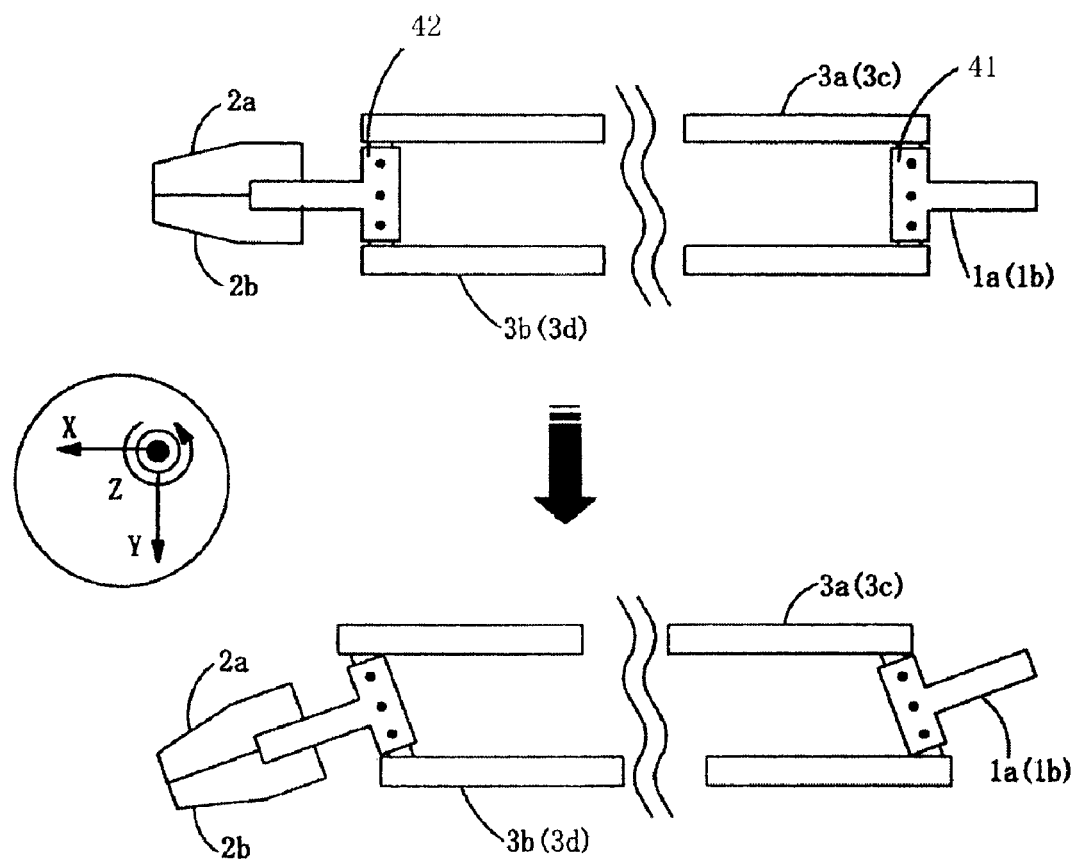
FIG. 7 is a view (3) illustrating a movement of the forceps of the embodiment of the present invention.

Referring to FIGS. 5 to 7 there are illustrated schematic views of describing the operation of the forceps of the present embodiment where an aspect of the gripping and changes of the pitch angle and yaw angle when the operating part 1 is controlled are shown.

FIG. 5 is a schematic view illustrating the movements of the working members 2a, 2b of the working part 2 when the operating members 1a, 1b of the operating part 1 are turned respectively.

The same figure (a) and (b) are views each illustrating the movements of the operating member 1a, the driving rods 3a, 3b on the upper side, and the working member 2a. As illustrated in the same figure (a) and (b) once the operating member 1a is turned, the driving rods 3a, 3b move as indicated by an arrow in the same figure and the working member 2a is turned as shown in the same figure. The same figure (c) is a view illustrating the movements of the operating member 1b, the driving rods 3c, 3d on a lower side, and the working member 2b. As illustrated in the same figure, once the operating member 1b is turned, the driving rods 3c, 3d move as indicated by an arrow in the same figure and the working member 2b is turned as shown in the same figure.

More specifically, the driving rods 3a to 3d move as shown in the same figure in response to opening and closing of the control members 1a, 1b, and in response to this the working members 2a, 2b are opened and closed.

It is hereby possible to grip an article with the working members 2a, 2b by controlling the operating members 1a, 1b.

The force acted on the working part 2 is transmitted to the operating members 2a, 2b via the driving rods 3a to 3d, and a worker can sense the force acted on the working part 2 as force sensation.

FIG. 6 is a schematic view illustrating the movement of the working part 2 when the pitch angle of the operating part 1 is changed.

Once the operating members 1a, 1b are turned as illustrated in the same figure to change the pitch angle, the driving rods 3b, 3d move as indicated by an arrow in the same figure, and so the working members 2a, 2b are turned as illustrated in the same figure to change the pitch angle. It is herein noticed that although the driving rods 3a, 3c are hidden behind the driving rods 3b, 3d and not seen in the same figure, the driving rod 3a moves in the same direction as that of the driving rod 3b and the driving rod 3c as that of the driving rod 3d.

FIG. 7 is a schematic view illustrating the movement of the working part 2 when the yaw angle of the operating part 1 is changed.

Once the operating members 1a, 1b are turned as illustrated in the same figure to change the yaw angle, the driving rods 3a, 3b move as shown by an arrow in the same figure, and so the working members 2a, 2b are turned as illustrated also in the same figure to change the pitch angle. It is herein noticed that although the driving rods 3c, 3d are hidden behind the driving rods 3a, 3b and not seen in the same figure, the driving rod 3a moves in the same direction as that of the driving rod 3c and the driving rod 3c in the same direction as that of the driving rod 3d.

Meanwhile, a forceps for use in the low invasion operation is configured into an elongated rod having a gripper part on the tip end of a shaft of about 300 mm ordinarily.

Provided that the forceps is increased in its length, the driving rods 3a to 3d are deflected for example when force is applied as described before, and so the operation force of the operating part 1 might be prevented from being correctly transmitted to the working part 2, and acted force on the working part 2 might be prevented from being correctly transmitted as force sensation.

In such a case, the coupling member 43 may be provided in the way of the driving rod as described previously. It is hereby possible to prolong the axial length of the forceps without substantially losing rigidity. It is further possible to prevent the coupling member 43 i.e. the driving rods 3a to 3d from moving with respect to the outer frame 6 by mounting the coupling member 43 on the fixing frame 51.

Figure 8:
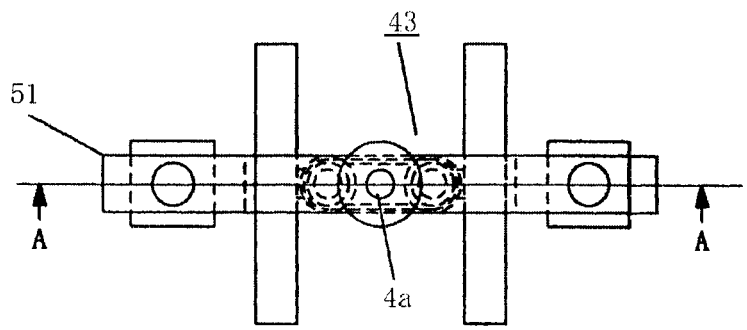
FIG. 8 is a view illustrating an exemplary constitution of a fixing member.
Figure 8:
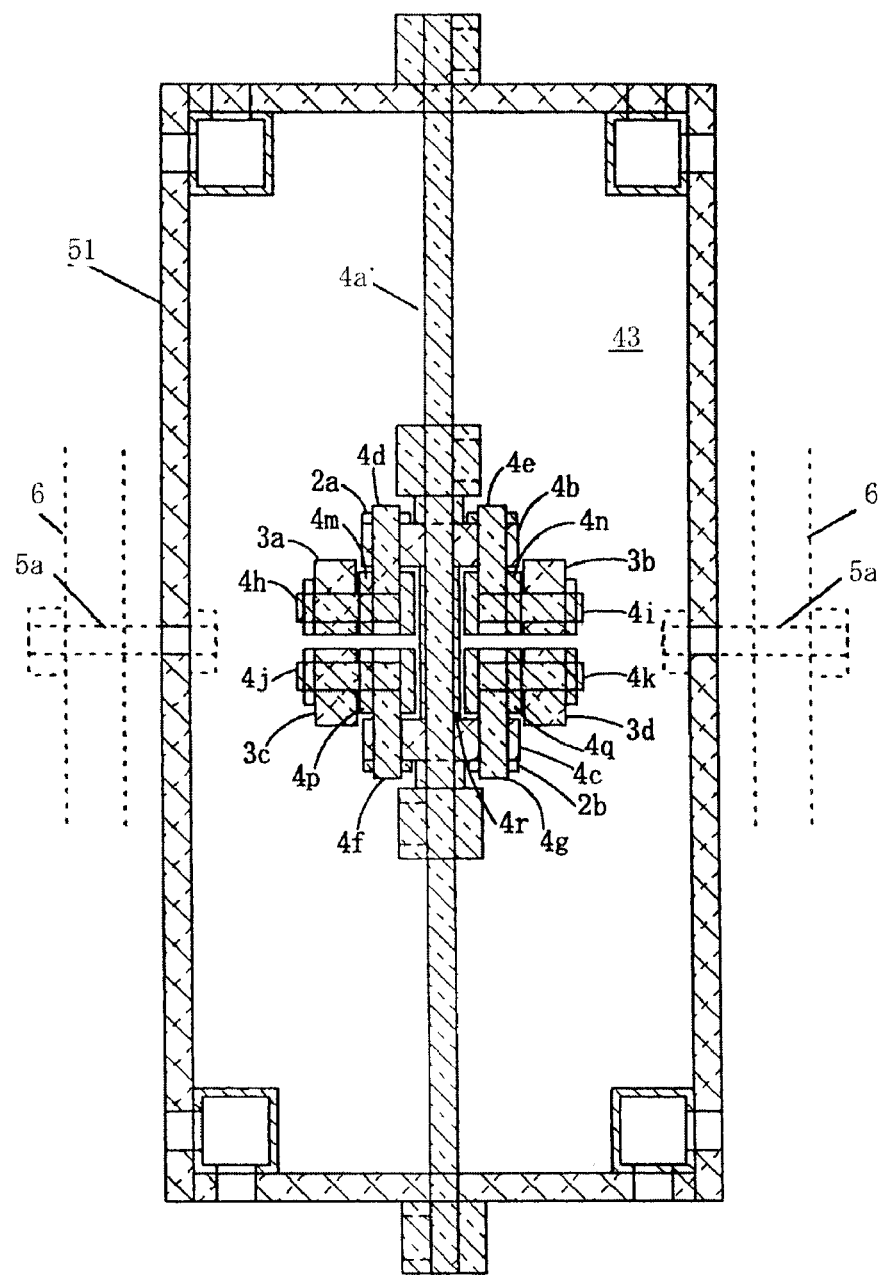

Referring to FIG. 8, there is illustrated an exemplary constitution of the fixing member composed of the coupling member 43 and the fixing frame 51, with (a) a view of the fixing frame 51 and the coupling member 43 seen from a Z-axis direction, and (b) a cross sectional view taken along A-A in (a).

In the same figure (b), the fixing frame 51 is mounted on the outer frame 6 via the shaft 5a and is turnable around the shaft 5a. The axial direction of the shaft 5a is parallel to Y-axis in FIG. 1.

Further, the central shaft 4a of the coupling member is attached to upper and lower frames of the fixing frame 51. For this, the coupling member 43 is turnable around the central shaft 4a.

Although the structure of the coupling member 43 is basically the same as those illustrated in FIGS. 3, 4, the coupling member 43 does not include the operating members 1a, 1b and the working members 2a, 2b, and the coupling rods 3a to 3d are mounted turnably on the first to fourth driving rod support shafts 4h to 4k of the coupling member 43, and further the driving rods 3a to 3d are extended to before and behind the coupling member 43 as illustrated in FIG. 8(a).

The movement of the coupling member 43 is the same as that illustrated in FIG. 4; once the driving rod 3a moves from the background in FIG. 8(b) and the driving rod 3b moves from the foreground to the background, the first movable member 4b is turned around the central shaft 4a. Similarly, once the driving rod 3d moves from the background in FIG. 8(b) toward the foreground and the driving rod 3c moves from the foreground toward the background, the second movable member 4c is turned around the central shaft 4a. Provided that the driving rods 3a to 3d move oppositely to the above situation, the first and second movable members 4b, 4c are turned oppositely.

Further, once the driving rods 3a, 3b move from the foreground in FIG. 8(b) toward the background and the driving rods 3c, 3d move from the background toward the foreground, the central shaft 4a, in FIG. 8(b), is tilted such that an upper side thereof becomes the background and a lower side thereof becomes the foreground, and the fixing frame 51 is also likewise tilted. Once the driving rods 3a to 3d move oppositely to the above description, the central shaft 4a is tilted such that an upper side thereof becomes the foreground and a lower side thereof becomes the background, and the fixing frame 51 is also likewise tilted.

Additionally, once the driving rods 3a, 3c move from the foreground in FIG. 8(b) toward the background and the driving rods 3b, 3d move from the background toward the foreground, the first and second movable members 4b, 4c are turned around the central shaft 4a. Once the driving rods 3a to 3d move oppositely to the above situation, the first and second movable members 4b, 4c are turned oppositely.

Herein, only the coupling member 43 may be provided without providing the fixing frame 51 as described previously. The situation is the same as the above description excepting a fact that the central shaft 4a of the coupling member 43 is not mounted on the fixing frame 51.

And now, endoscopic operation sometimes suffers from a problem of gripping force. When there is a need of increasing gripping force at the working part of the forceps, it is possible to realize an increase of the gripping force by mounting a link mechanism on the tip ends of the first and second working members.

Figure 9:
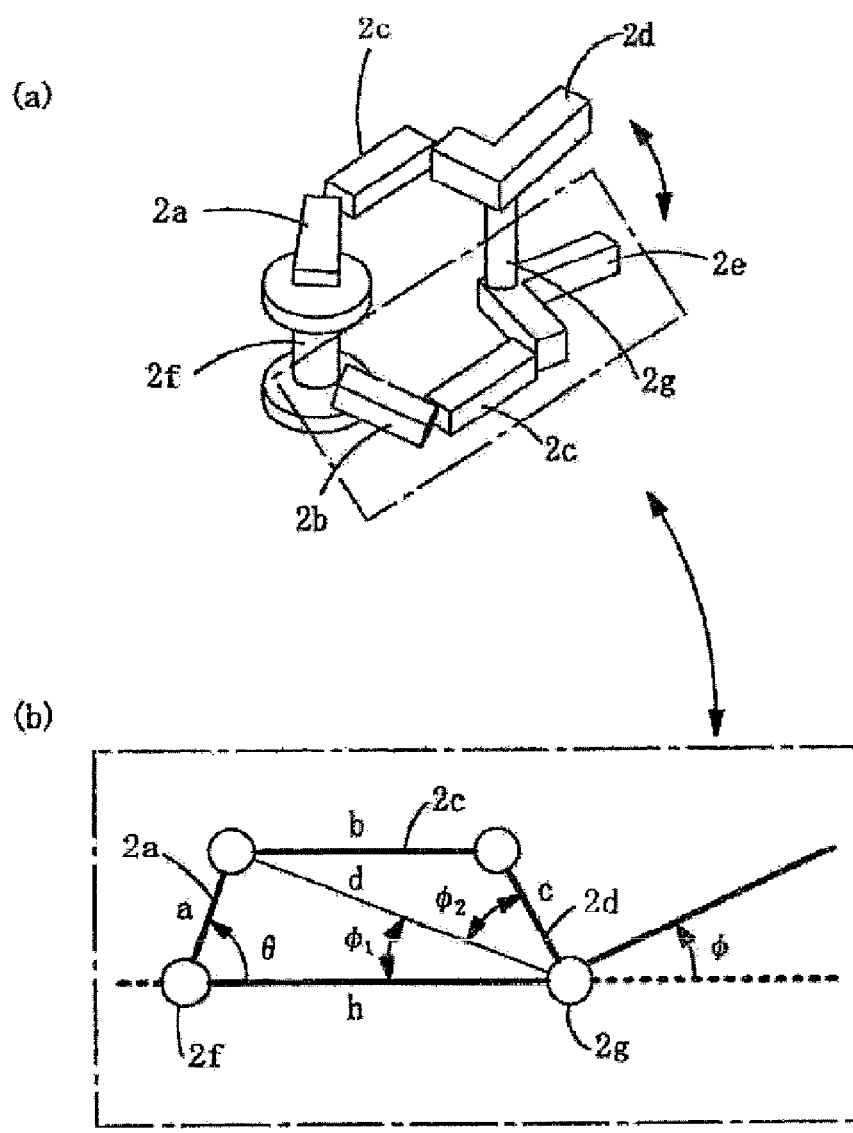
FIG. 9 is a view illustrating a link mechanism mounted on a tip end of a working member.

FIG. 9(a) is a view illustrating a schematic constitution of the link mechanism. An arm 2c is mounted on the tip ends of the first and second working members 2a, 2b of the working part, and "L"-shaped third and fourth working members 2d, 2e are mounted on the arm 2c.

The first and second working members 2a, 2b are turned around a rotary shaft 2f, and the upper and lower arms 2cs are coupled turnably with the first and second working members 2a, 2b. Further, the third and fourth working members 2d, 2e are mounted turnably around a rotary shaft 2g parallel, in its axial direction, to the rotary shaft 2f, and each of the arms 2c is turnably coupled with one ends of the third and fourth working members 2d, 2e. The other ends of the third and fourth working members 2d, 2e are the gripping part for gripping an article.

FIG. 9(b) illustrates a mechanism composed of the first and third working members of the link mechanism; the first and second working members 2a, 2b are equal to each other in length, likewise, upper and lower arms 2cs, third and fourth working members 2d, 2e are all equal to each other in their lengths. The length of the first working member 2a (2b) is assumed to be a; the length of the arm 2cb; the length of the third working member 2d (2e) from the rotary shaft 2g to the coupling part of the arm 2cc; a distance between the rotary shaft 2f of the working member 2a and the rotary shaft 2g of the third working member 2dh; an angle formed between a line connecting between the rotary shaft 2f and the rotary shaft 2g and the first working member 2a θ; and an angle formed between a line connecting the rotary shaft 2f and the rotary shaft 2g and a line connecting the rotary shaft 2g of the working member 2d (2e) and its tip end φ, which satisfy the following relations:

$$d^2 = a^2 + h^2 - 2ah \cos \theta$$

$$\pi/2 - \phi = \phi 1 + \phi 2$$

$$a^2 = d^2 + h^2 - 2dh \cos \phi 1$$

$$b^2 = d^2 + c^2 - 2dc \cos \phi 2$$

Figure 10:
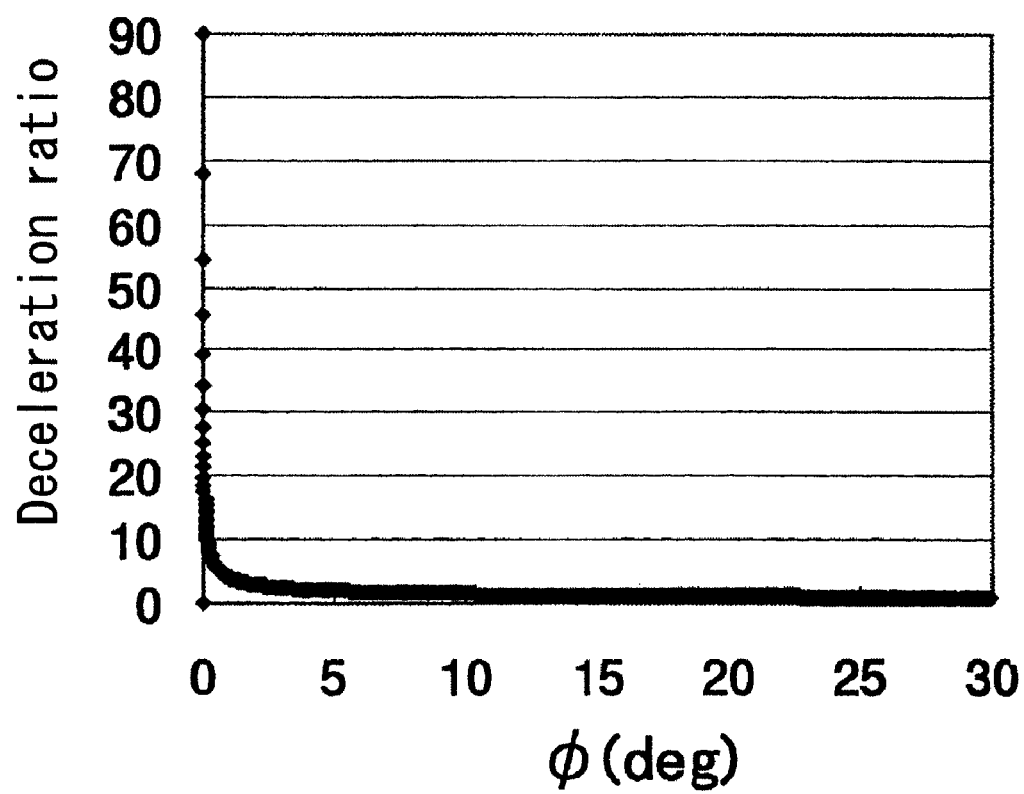
FIG. 10 is a view illustrating a deceleration ratio by the link mechanism.

FIG. 10 is a view illustrating a relationship between the foregoing φ and reduction gear ratios of the third and fourth working members 2d, 2e with respect to the first and second working parts 2a, 2b. It is possible to reduce the speed of the third and fourth working members 2d, 2e as φ is more reduced as illustrated in FIG. 10 and hence to increase the force applied to the third and fourth working members 2d, 2e by setting the length b of the arm 2c and the distance h between the rotary shaft 2f of the working member 2a and the rotary shaft 2g of the working member 2d to satisfy a relation: b<h and making the shape of a rectangle formed by the length b and the distance h a trapezoid as illustrated in FIG. 9(b).

For this, it is possible to increase the gripping force when a needle or the like is gripped at the tip end of the forceps for example and improve operationability. Additionally, it is possible to shift a rotary article (rotary shaft 2f) and an axis of gripping (rotary shaft 2g) and hence improve the operationability by providing the link mechanism. Furthermore, it is also possible to reduce an influence of friction because the force can be increased.

The forceps of the present embodiment, as described above, transmits an input to the operating part 1 to the working part 2 (the tip end of the forceps) through the four driving rods 3a to 3d, and the forceps of the present embodiment has the following features:

(1) All degrees of freedom of the three-degree-of-freedom can be realized by only the link mechanism composed of the four driving rods. Manipulators of a parallel link structure are ones that consider only a position of a tip end thereof and an attitude thereof, and many of them incorporate a terminal effector such as a gripper and a drill at the tip end thereof and realize the freedom of the gripper not by a link but by wires and springs. So, when a forceps is directly operated, an operator feels elasticity of the spring and friction of the wire, which is not preferable. Also, they have the difficulty that any material is worn away by the friction of the wire.

Against this, the forceps of the present embodiment employs the link mechanism using the four driving rods 3a to 3d, so that the foregoing difficulty does not happen.

(2) The two-degree-of-freedom of rotation and the shaft axis of the forceps intersect at one point. Consequently, the turning around the roll shaft at the tip end of the forceps is enabled by the cooperation of the turning around the shaft axis and the pitch. This ensures excellent operationability and complicated control.

(3) When the article angle of the tip end of the forceps is changed, there is no chance of portions of the forceps other than the tip end being deformed such as other portions of forceps being protruded. Accordingly, when the forceps is applied to a low invasion operation for example, there is no chance of the shape of the forceps being changed outside the scope of an endoscope and hence there is no possibility of any organ or the like being caught up by the forceps.

Table 1 illustrates differences among the forceps of the present invention, the forcipes of the references 2 and 3, and the prior art forceps (having four-degree-of-freedom+gripping).

TABLE 1

|  | Ref. 2 | Ref. 3 | Forceps of the present invention | Conventional Forceps |
| --- | --- | --- | --- | --- |
| Degree of Freedom | 6 + 1 (gripping) | 6 + 1 (gripping) | 6 + 1 (gripping) | 4 + 1 (gripping) |
| Force Sensation | Nil | Medium | High | High |
| Cost | Expensive (Some hundred millions yen) | Relative Expensive (Some million yen) | Relatively Inexpensive | Inexpensive (some hundred thousand yen) |
| Advantageous in Introduction & Operation | Low | Medium | High | High |

As understood from Table 1, the forceps of the present invention enjoys the following effects: it is possible to transmit force sensation inexpensively while having the same degree of freedom as those of the forceps disclosed in reference 2 and reference 3; it is inexpensive and is advantageous in the aspect of the introduction and operation thereof; and further it has higher degree of freedom and greater controllability than the prior art forceps.

Table 2 illustrates features of the forceps of the present invention and the forceps of references 2 to 6 from the aspect of the operationability of the forceps.

TABLE 2

|  | Ref. 2 | Ref. 3 | Ref. 4 | Refs 5&6 | Forceps of the present invention |
| --- | --- | --- | --- | --- | --- |
| Do rotary shafts of two-degree-of-freedom at the tip end intersect? | No | Yes | No | Yes | Yes |
| Free from influence of static friction by wire? | No | No | Yes | Partially Yes* | Yes |
| Without Protruded portion upon bending? | Yes | Yes | No | Yes | Yes |
| Rigidity of force transmission method | No | No | Yes | Partially Yes* | Yes |

*on the condition that only gripping utilizes wire.

As shown in Table 2, the forceps of the present invention has higher operationability because rotary axes of the two-degree-of-freedom of rotation at the tip end of the forceps of the present invention intersect and it is less influenced by static friction compared with those utilizing wires because whole freedom is constituted by a link.

Additionally, there is no possibility that any other article than the aimed is caught up by the forceps because no bulged part could be occurred to the link mechanism at the time of bending of the tip end of the forceps, and the forceps has a fast force response because it adopts a link mechanism with higher rigidity than that of a wire.

Moreover, the forceps of the present embodiment is successful to pass through a cylinder of 12 mm. This is a size with which we can pass through an existing trocars, and which can be said as a practical size. For a movable range on design the change of the yaw angle is ±75°, the change of the pitch angle is ±60°, gripping ranges from 0° to 30°, so that it is possible to grip and lift up a weight of 410 grams.

It is generally said that if a forceps can generate force of about 4N, then it is applicable to low invasion operations. The developed forceps has enough rigidity against generated force necessary for a work in an abdominal cavity.

For checking the availability of the forceps of the present embodiment a correspondence of freedoms of the operating part of the forceps and of the tip end of the forceps was measured, and it was measured how much the force applied to the tip end of the forceps is transmitted to the operating part.

For checking a correspondence between movements of the operating part and of the tip end of the forceps, the operating part and the tip end of the forceps were simultaneously photographed using a home digital video camera to check the correspondence.

Figure 11:
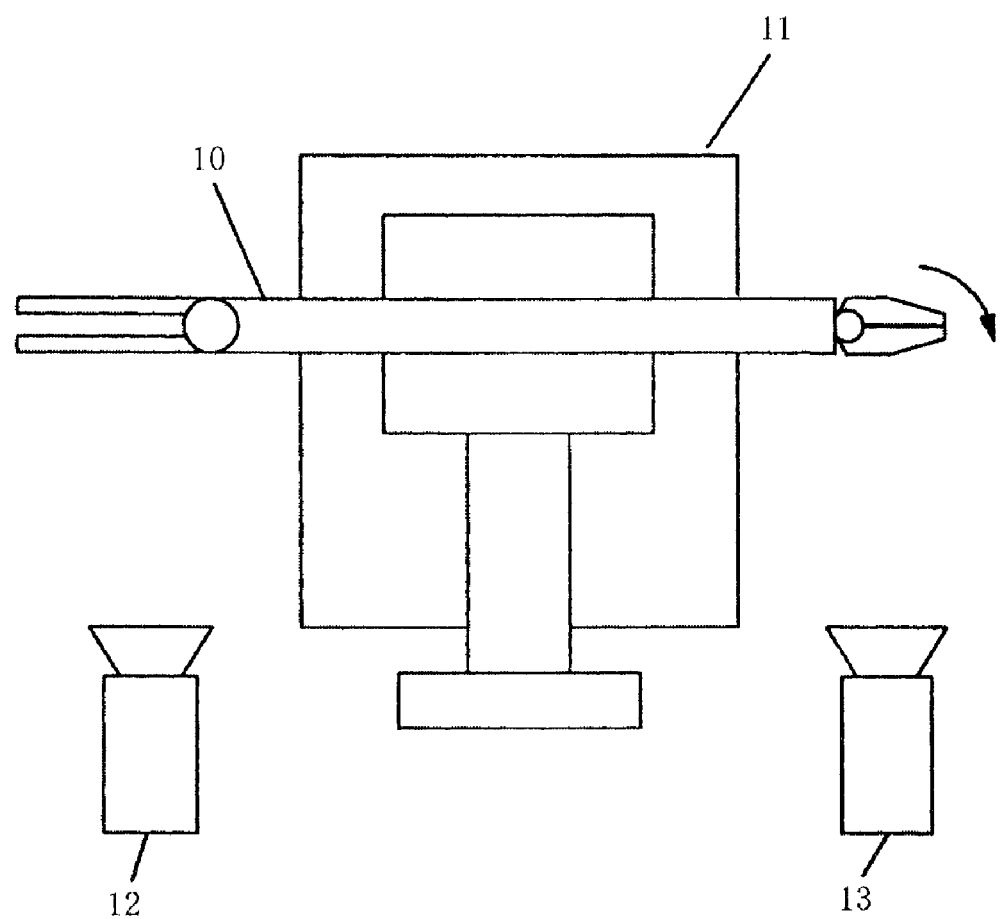
FIG. 11 is a view illustrating a constitution of an apparatus for measuring movements of the Operating Part (OPT) and the Tip End of the Forceps (TOF)

As shown in FIG. 11, the forceps 10 was photographed with video cameras 12, 13 in its state where it was fixed to a vise 11 at its shaft part.

Figure 12:
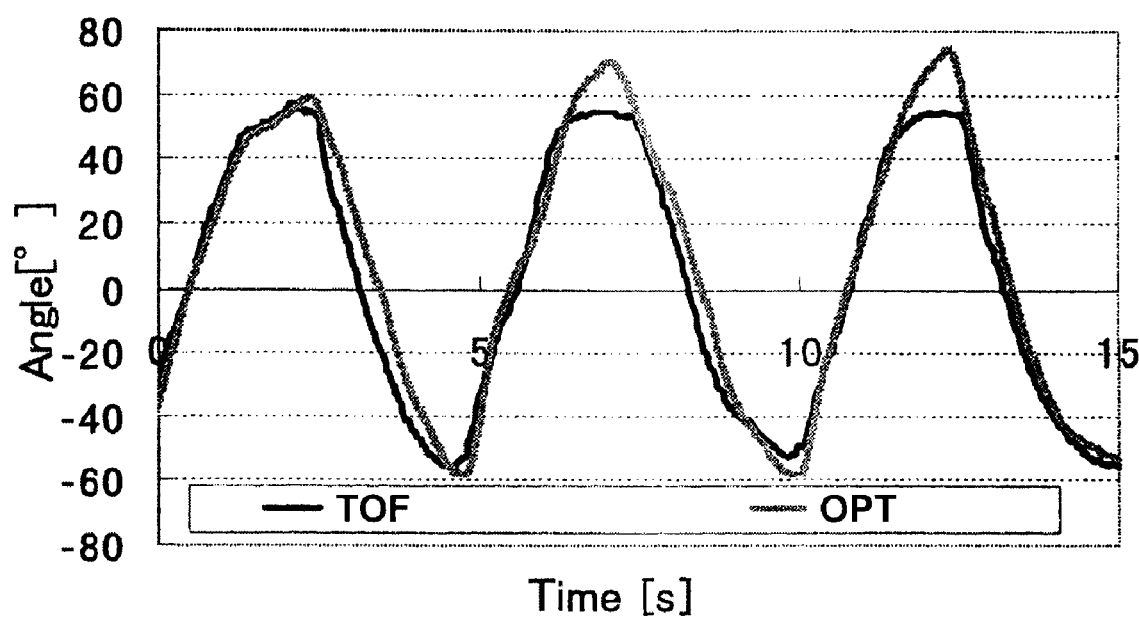
FIG. 12 is a view illustrating a measurement result of yaw angles of the OPT and the TOF.
Figure 13:
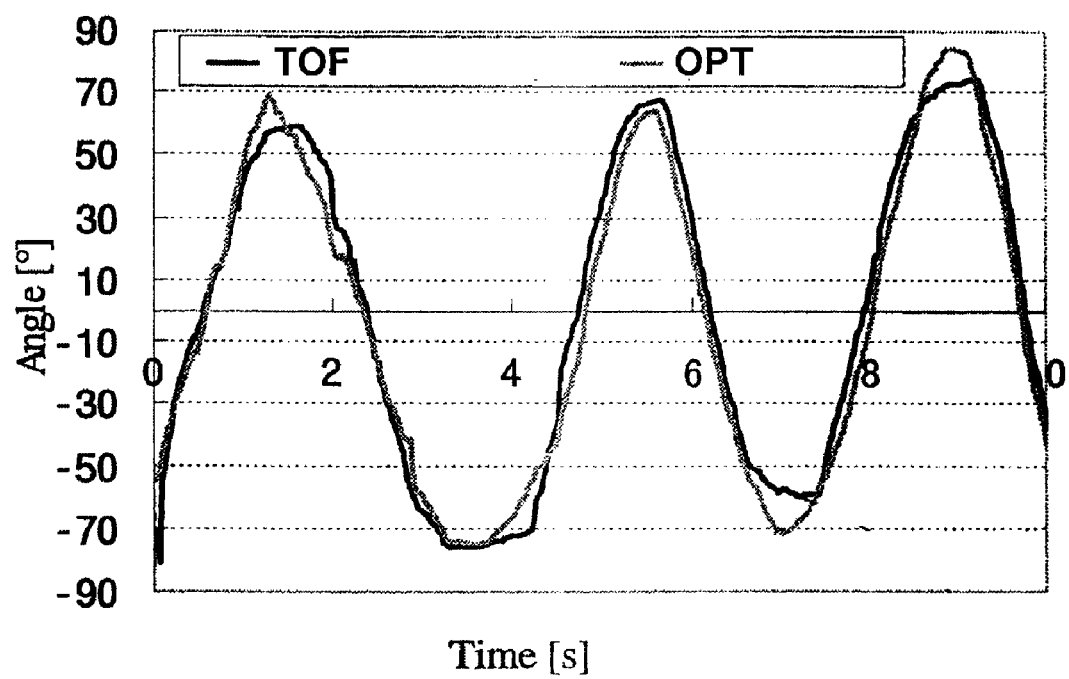
FIG. 13 is a view illustrating a measurement result of pitch angles of the OPT and the TOF.
Figure 14:
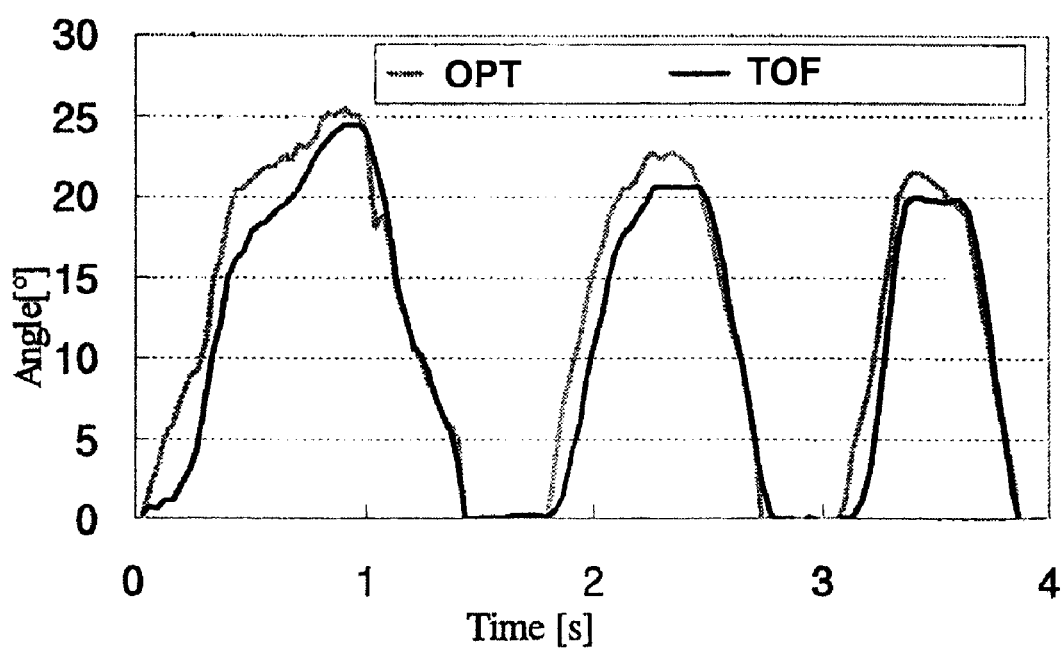
FIG. 14 is a view illustrating a measurement result of gripping of the OPT and the TOF.

A marker is detected by template matching from a photographed image, and attitudes of the tip and of the forceps and of the control part are calculated from coordinates of the maker. At that time, the forceps 10 is assumed to move on a two-dimensional plane, and a geometrical relation of the cameras 12, 13 is assumed to be parallel projection. A frame rate is 30.0 fps with a resolution of 740×480. Synchronization was taken by simultaneously lighting LEDS in two images, FIGS. 12 to 14 illustrate respective measurement results of the yaw, pitch, and gripping. The abscissa in the same figures is time(s) and the ordinate is angle (°), which indicate the movements of the operating part and the tip end of the forceps (working part). As illustrated in the same figures it is understood that for the yaw, pitch, and gripping the movement of the tip end of the forceps substantially corresponds to that of the tip end of the forceps.

However, hysteresis characteristics by an influence of backlash are found, causing a deviation of 15° at the maximum.

Figure 15:
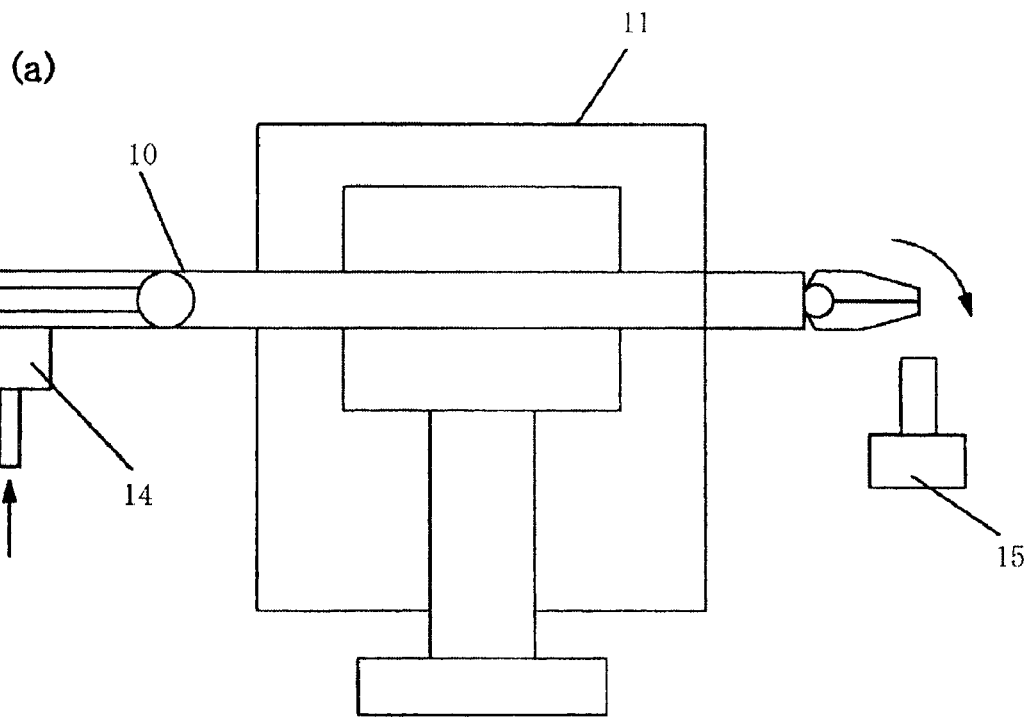
FIG. 15 is a view illustrating a constitution of an apparatus for measuring force transmission characteristics.
Figure 15:
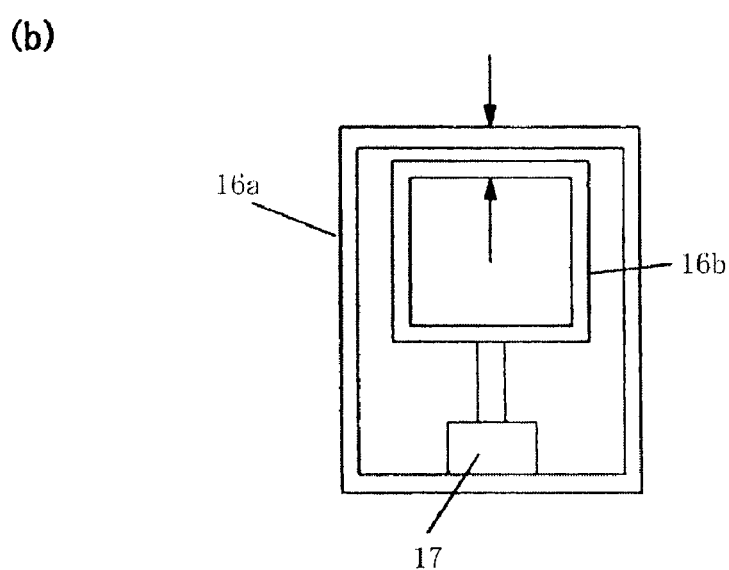

As shown in FIGS. 12 and 13, even if deviations between the operating part and the tip end of the forceps are increased at upper end peaks of waves and at lower end peaks of the same, those peaks for the tip end of the forceps have not been changed. This is considered that the reason is because an actual movable range is narrower than the designed one, Then, force transmission performance was measured. As shown in FIG. 15(a) force transmitted from the tip end of the forceps or force transmitted from the operating part to the operating part or to the tip end of the forceps was measured by operating the operating part while measuring force of the operating part by mounting a force sensor 14 on the operating part, and by making the tip end of the forceps contact with a force sensor 15.

This experiment was also implemented in the state where the forceps 10 was fixed to a vise 11 as a shaft part thereof. When the gripping force is measured, the measurement was implemented by mounting two square pipes 16a, 16b on a force sensor 17 as illustrated in FIG. 15(b).

Figure 16:
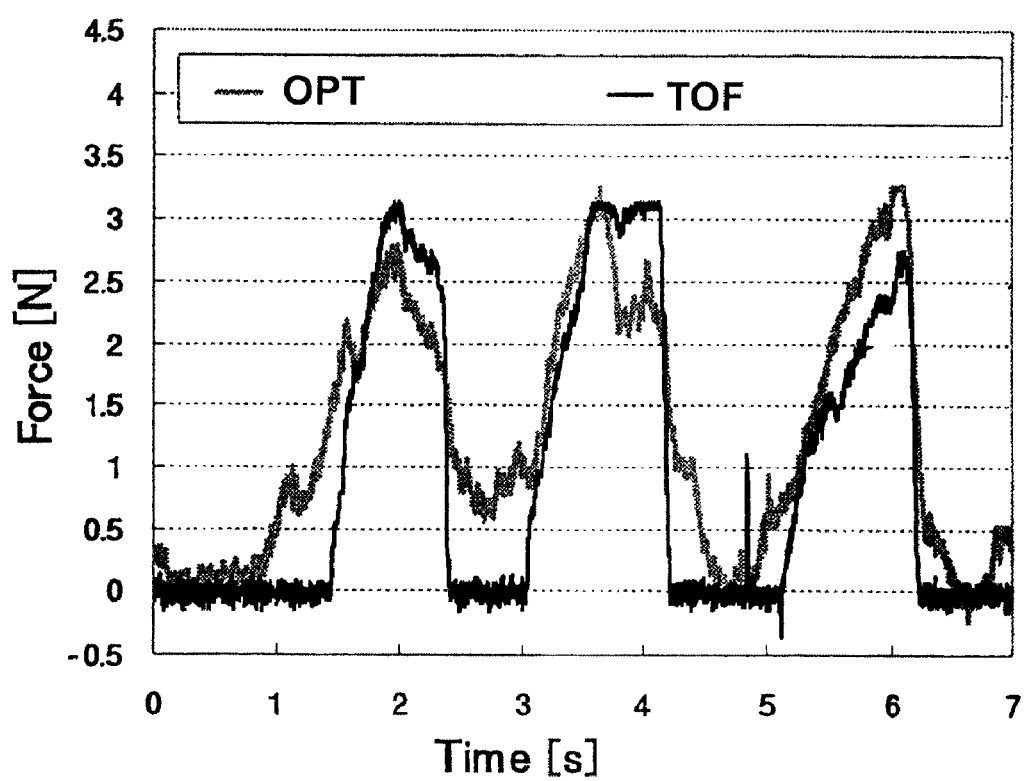
FIG. 16 is a view illustrating a measurement result of force transmission characteristics (yaw) of the OPT and the TOF.
Figure 17:
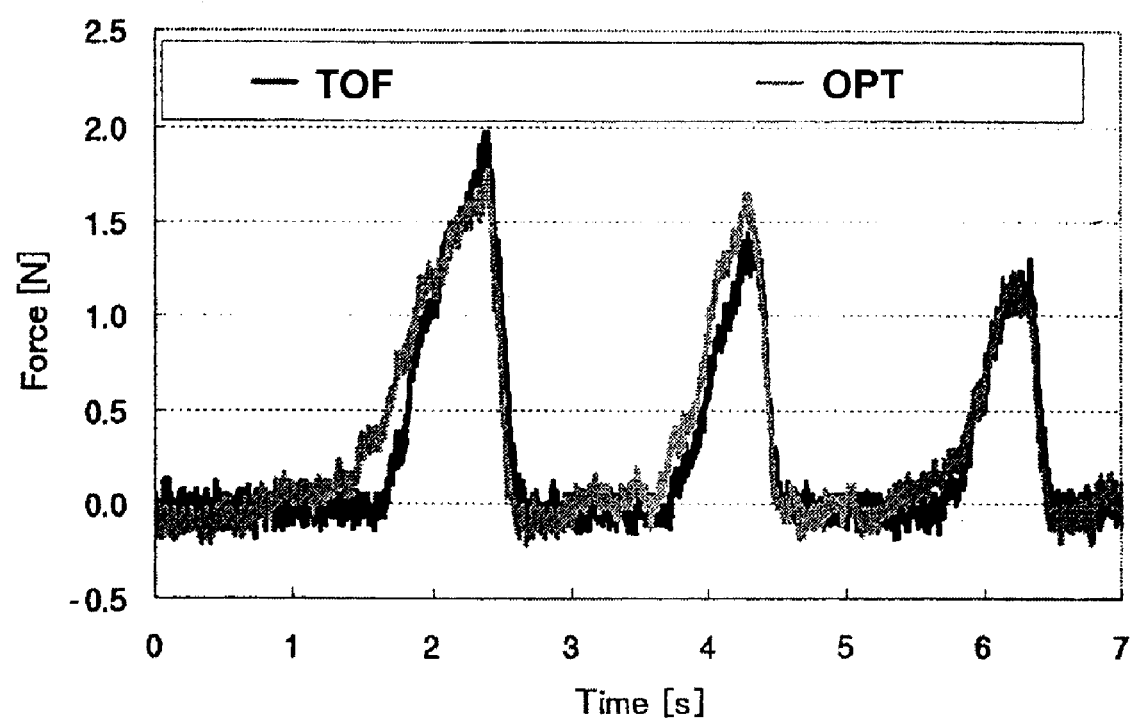
FIG. 17 is a view illustrating a measurement result of force transmission characteristics (pitch) of the OPT and the TOF.
Figure 18:
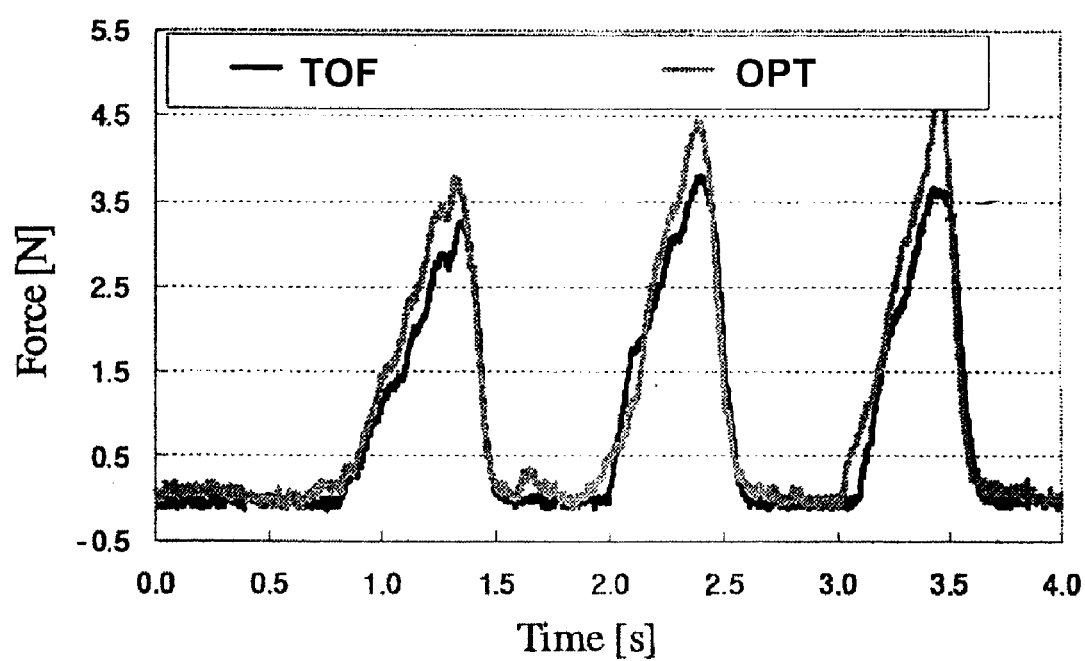
FIG. 18 is a view illustrating a measurement result of force transmission characteristics (gripping) of the OPT and the TOF.

FIGS. 16 to 18 illustrate respective measurement results of the yaw, pitch, and gripping. In the same figures, the abscissa is time (s) and the ordinate is force (N) that indicates force acting on the operating part and on the tip end of the forceps (working part).

It is understood from the same figure that generated force at the tip end of the forceps follows up applied force to the operating part. However, it can be read out that the generated force at the tip end of the forceps is retarded with respect to the applied force to the operating part. The deviation of the forces at the operating part and the tip end of the forceps was 1N at the maximum. Particularly, it can be read that the degree of freedom of the yaw angle is severely influenced by friction and backlash.

What is claimed is:

1. A manipulator including a working part for implementing a work and an operating part for implementing an operation, the operation in the said operating part being transmitted to the said working part, and force acted on the said working part being transmitted to the said operating part as force sensation comprising:

at least four driving rods provided between said working part and said operating part;

opposite ends of said driving rod coupled with said working part and said operating part via coupling members of the same structure;

longitudinal axes of said respective driving rods are directed in parallel and at least longitudinal axes of all the driving rods being arranged not to be in the same plane; and said coupling members on sides of the operating part and said working part forcing said respective driving rods to be moved axially in conformity with the operation said the operating part while keeping them in parallel and driving said working part correspondingly to the operation of said operation part, each of said coupling members having a central axis;

wherein said operating part comprises a first and a second operating member, said first and said second operating member being coupled rotatably to said coupling member on the side of said operating part taking said central axis of said coupling member on the side of said operating part as an axis, said working part comprises a first and a second working member, and said first and said second working member being coupled rotatably with said coupling member of the side of said working part taking said central axis of said coupling member as an axis;

at least a first and a third driving member of said driving rods are coupled with one side of said coupling member with respect to said central axis respectively independently rotatably, and at least a second and a fourth driving member of said driving rods are coupled with the other side of said coupling member with respect to said central axis respectively independently rotatably;

a first operating member is coupled with said first working member via a first and a second driving rod of said four driving rods, and said second operating member being coupled with said second working member via a third and a fourth driving rod of said four driving rods;

when it is assumed that the direction of the axis of said driving rods is an X axis direction, and directions perpendicular to the X-axis are Y-axis and Z-axis directions respectively, when said first and said second operating member are both rotated around the Y-axis, at least said first and said second driving rod are both rotated in a first direction via said coupling member, and said third and said fourth driving rod move oppositely to said first direction to both rotate said first and said second working members around the Y-axis;

when said first and said second operating members are both rotated around Z-axis, at least said first and said third driving rod are both rotated in a first direction, and said second and said fourth driving rod move oppositely to said first direction to both rotate said first and said second working member;

when said first operating member is rotated around Z-axis, one of said first and said second driving rod is rotated in a first direction and the other moves in the opposite direction to rotate said first working member around Z-axis; and when said second operating member is rotated around Z-axis, one of said third and said fourth driving rod is rotated in the first direction and the other moves in the opposite direction to the first direction to rotate said second working member around Z-axis.

2. The manipulator according to claim 1, wherein said first coupling member includes a first and a second movable member rotatable around said central axis thereof;

said second coupling member includes a third and a fourth movable member rotatable around said central axis thereof;

said first operating member is coupled to said first movable member;

said second operating member is coupled to said second movable member;

said first working member is coupled to said third movable member;

said second working member is coupled to said fourth movable member;

said first driving rod is provided between each one side of said first movable member and said third movable member with respect to said central axis, rotatably around a first axis parallel to said central axis, and rotatably around a second axis perpendicular to both said central axis and the longitudinal direction of said first driving rod;

said second driving rod is provided between each the other side of said first movable member and said third movable member with respect to said central axis, rotatably around a third axis parallel to said central axis, and rotatably around a fourth axis perpendicular to both said central axis and the longitudinal direction of said second driving rod;

said third driving rod is provided between each one side of said second movable member and said fourth movable member with respect to said central axis, rotatably around a fifth axis parallel to said central axis, and rotatably around a sixth axis perpendicular to both said central axis and the longitudinal direction of said third driving rod; and said fourth diving rod is provided between each the other side of said second movable member and said fourth movable member with respect to said central axis, rotatably around a seventh axis parallel to said central axis, and rotatably around a eighth axis perpendicular to both said central axis and the longitudinal direction of said fourth driving rod.

3. The manipulator according to claim 1 wherein one or more intermediate coupling members having the central axis, with the same structure as each of said first coupling member and said second coupling member, is provided in each way of said driving rods, thereby supporting said driving rods.

4. The manipulator according to claim 2 wherein one or more intermediate coupling members having the central axis, with the same structure as each of said first coupling member and said second coupling member, is provided in each way of said driving rods, thereby supporting said driving rods.

5. The manipulator according to claim 3, comprising:
a easing for covering said driving rods; and
a fixing member attached to said easing rotatably around said Y axis;
wherein at least one of said intermediate coupling members is mounted on said fixing member, said central axis thereof being in said Z-axis direction.

6. The manipulator according to claim 1, wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working member, and having the other end side thereof rotatably mounted on said first working member;
a second arm having one end side thereof rotatably mounted on said other side of said fourth working member, and having the other end side thereof rotatably mounted on said second working member; and wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

7. The manipulator according to claim 2, wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working member (2*d*), and having the other end side thereof rotatably mounted on said first working member;
a second arm having one end side thereof rotatably mounted on said other side of said fourth working member, and having the other end side thereof rotatably mounted on said second working member; and
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

8. The manipulator according to claim 3, wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working member, and having the other end side thereof rotatably mounted on said first working member;
a second arm having one end side thereof rotatably mounted on said other side of said fourth working member, and having the other end side thereof rotatably mounted on said second working member;
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

9. The manipulator according to claim 5, wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working member, and having the other end side thereof rotatably mounted on said first working member;
a second arm having one end side thereof rotatably mounted on said other side of said fourth working member, and having the other end side thereof rotatably mounted on said second working member; and
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

10. A manipulator including a working part for implementing a work and an operating part for implementing an operation, the operation in said operating part being transmitted to said working part, and force acted on said working part being transmitted to said operating part as force sensation comprising:
a first, second, third and fourth driving rods, in total four driving rods, are provided between said working part and said operating part;
a first coupling member on said operating part and a second coupling member on said working part, of the same structure, are provided to couple said driving rods with said operating part and said working part, each of said first coupling member and said second coupling member having a central axis;
opposite ends of said respective driving rods are coupled with said operating part and said working part via said first coupling member and said second coupling member;
longitudinal axes of said respective driving rods are directed in parallel and at least longitudinal axes of all the driving rods being arranged not to be on the same plane; and
said first coupling member and said second coupling member forcing said respective driving rods to move axially in conformity with the operation of said operating part while keeping them in parallel and driving said working part correspondingly to the operation of said operating part;
said operating part comprises a first and a second operating member, said first and said second operating member being coupled rotatably, independently from each other, to said first coupling member;
said working part comprises a first and a second working member, said first and said second working member being coupled rotatably, independently from each other, to said second coupling member;
said first operating member and said first working member are coupled via said first and said second driving rod provided between said first coupling member and said second coupling member; and
said second operating member and said second working member are coupled via said third and said fourth driving rod provided between said first coupling member and said second coupling member,
wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working member, and having the other end side thereof rotatably mounted on said first working member;
a second arm having one end side thereof rotatably mounted on said other side of said fourth working member,
and having the other end side thereof rotatably mounted on said second working member; and
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

11. A manipulator including a working part for implementing a work and an operating part for implementing an operation, the operation in said operating part being transmitted to said working part, and force acted on said working part being transmitted to said operating part as force sensation comprising:
a first, second, third and fourth driving rods, in total four driving rods, are provided between said working part and said operating part;
a first coupling member on said operating part and a second coupling member on said working part, of the same structure, are provided to couple said driving rods with said operating part and said working part, each of said first coupling member and said second coupling member having a central axis;
opposite ends of said respective driving rods are coupled with said operating part and said working part via said first coupling member and said second coupling member;
longitudinal axes of said respective driving rods are directed in parallel and at least longitudinal axes of all the driving rods being arranged not to be on the same plane; and
said first coupling member and said second coupling member forcing said respective driving rods to move axially in conformity with the operation of said operating part while keeping them in parallel and driving said working part correspondingly to the operation of said operating part;
said operating part comprises a first and a second operating member, said first and said second operating member being coupled rotatably, independently from each other, to said first coupling member;

said working part comprises a first and a second working member, said first and said second working member being coupled rotatably, independently from each other, to said second coupling member;
said first operating member and said first working member are coupled via said first and said second driving rod provided between said first coupling member and said second coupling member; and
said second operating member and said second working member are coupled via said third and said fourth driving rod provided between said first coupling member and said second coupling member,
wherein said first coupling member includes a first and a second movable member rotatable around said central axis thereof;
said second coupling member includes a third and a fourth movable member rotatable around said central axis thereof;
said first operating member is coupled to said first movable member;
said second operating member is coupled to said second movable member;
said first working member is coupled to said third movable member;
said second working member is coupled to said fourth movable member;
said first driving rod is provided between each one side of said first movable member and said third movable member with respect to said central axis, rotatably around an first axis parallel to said central axis, and rotatably around an second axis perpendicular to both said central axis and the longitudinal direction of said first driving rod;
said second driving rod is provided between each the other side of said first movable member and said third movable member with respect to said central axis, rotatably around a third axis parallel to said central axis, and rotatably around a fourth axis perpendicular to both said central axis and the longitudinal direction of said second driving rod;
said third driving rod is provided between each one side of said second movable member and said fourth movable member with respect to said central axis, rotatably around a fifth axis parallel to said central axis, and rotatably around a sixth axis perpendicular to both said central axis and the longitudinal direction of said third driving rod; and
said fourth driving rod is provided between each the other side of said second movable member and said fourth movable member with respect to said central axis, rotatably around an seventh axis parallel to said central axis, and rotatably around a eighth axis perpendicular to both said central axis and the longitudinal direction of said fourth driving rod, and
wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;

a first arm having one end side thereof rotatably mounted on said other end side of said third working member, and having the other end side thereof rotatably mounted on said first working member;
a second arm having one end side thereof rotatably mounted on said other side of said fourth working member, and having the other end side thereof rotatably mounted on said second working member; and
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

12. A manipulator including a working part for implementing a work and an operating part for implementing an operation, the operation in said operating part being transmitted to said working part, and force acted on said working part being transmitted to said operating part as force sensation comprising:
a first, second, third and fourth driving rods, in total four driving rods, are provided between said working part and said operating part;
a first coupling member on said operating part and a second coupling member on said working part, of the same structure, are provided to couple said driving rods with said operating part and said working part, each of said first coupling member and said second coupling member having a central axis;
opposite ends of said respective driving rods are coupled with said operating part and said working part via said first coupling member and said second coupling member;
longitudinal axes of said respective driving rods are directed in parallel and at least longitudinal axes of all the driving rods being arranged not to be on the same plane; and
said first coupling member and said second coupling member forcing said respective driving rods to move axially in conformity with the operation of said operating part while keeping them in parallel and driving said working part correspondingly to the operation of said operating part;
said operating part comprises a first and a second operating member, said first and said second operating member being coupled rotatably, independently from each other, to said first coupling member;
said working part comprises a first and a second working member, said first and said second working member being coupled rotatably, independently from each other, to said second coupling member;
said first operating member and said first working member are coupled via said first and said second driving rod provided between said first coupling member and said second coupling member; and
said second operating member and said second working member are coupled via
said third and said fourth driving rod provided between said first coupling member and said second coupling member,
wherein one or more intermediate coupling members having the central axis, with the same structure as each of said first coupling member and said second coupling member, is provided in each way of said driving rods, thereby supporting said driving rods, and wherein a link mechanism is used in said working part;
said link mechanism comprising:
a rotation axis parallel to said central axis of said second coupling member;
a third working member pivoting around said rotation axis and having one free end side acting as a first gripping constituent element of an article to be worked, and having the other end side;
a fourth working member pivoting around said rotation axis and having one free end side acting as a second gripping constituent element of said article to be worked, and having the other end side;
a first arm having one end side thereof rotatably mounted on said other end side of said third working in ember, and having the other end side thereof rotatably mounted on said first working member;
a second arm having one end side thereof rotatably mounted on said other side of said fourth working member, and having the other end side thereof rotatably mounted on said second working member; and
wherein a configuration obtained by connecting four points of said central axis, said rotation axis and respective rotation central axes at opposite ends of said first arm, and a configuration obtained by connecting four points of said central axis, said rotation axis and respective rotation central axes at opposite ends of said second arm are a rectangle, respectively.

* * * * *